(12) United States Patent
McGirt

(10) Patent No.: US 10,499,969 B2
(45) Date of Patent: Dec. 10, 2019

(54) BONE FIXATION SCREW WITH DEPLOYABLE ANCHORS

(71) Applicant: Matthew J. McGirt, East Charlotte, NC (US)

(72) Inventor: Matthew J. McGirt, East Charlotte, NC (US)

(73) Assignee: MiRus, LLC, Marietta, GA (US)

(*) Notice: Subject to any disclaimer, the term of this patent is extended or adjusted under 35 U.S.C. 154(b) by 184 days.

(21) Appl. No.: 15/793,024

(22) Filed: Oct. 25, 2017

(65) Prior Publication Data

US 2018/0140340 A1    May 24, 2018

Related U.S. Application Data

(60) Provisional application No. 62/418,533, filed on Nov. 7, 2016.

(51) Int. Cl.

| | |
|---|---|
| *A61B 17/04* | (2006.01) |
| *A61B 17/86* | (2006.01) |
| *A61F 2/08* | (2006.01) |
| *A61B 17/84* | (2006.01) |
| *A61B 17/68* | (2006.01) |

(52) U.S. Cl.
CPC .......... *A61B 17/864* (2013.01); *A61B 17/846* (2013.01); *A61B 17/8605* (2013.01); *A61B 17/8685* (2013.01); *A61B 17/683* (2013.01); *A61B 2017/0412* (2013.01)

(58) Field of Classification Search
CPC combination set(s) only.
See application file for complete search history.

(56) References Cited

U.S. PATENT DOCUMENTS

2010/0057141 A1*  3/2010  Abdelgany ........ A61B 17/8685
                                                           606/310

* cited by examiner

*Primary Examiner* — Sameh R Boles
(74) *Attorney, Agent, or Firm* — Eric B. Fugett; Mark A. Pitchford; Pitchford Fugett, PLLC

(57) ABSTRACT

A bone fixation screw device for implantation into a bone of a patient is disclosed. The screw device includes a screw body having an outer surface. A plurality of outer screw threads extends around the outer surface of the screw body. A plurality of apertures or passages is defined through the outer surface. A plurality of anchors can extend out of corresponding apertures in the screw body. The anchors can be inserted into a patient's bone to further fixate and purchase the bone screw within the patient's bone. The screw body can include an inner cavity, the plurality of apertures each being open to the inner cavity. The anchors can extend out of corresponding apertures from the inner cavity.

19 Claims, 19 Drawing Sheets

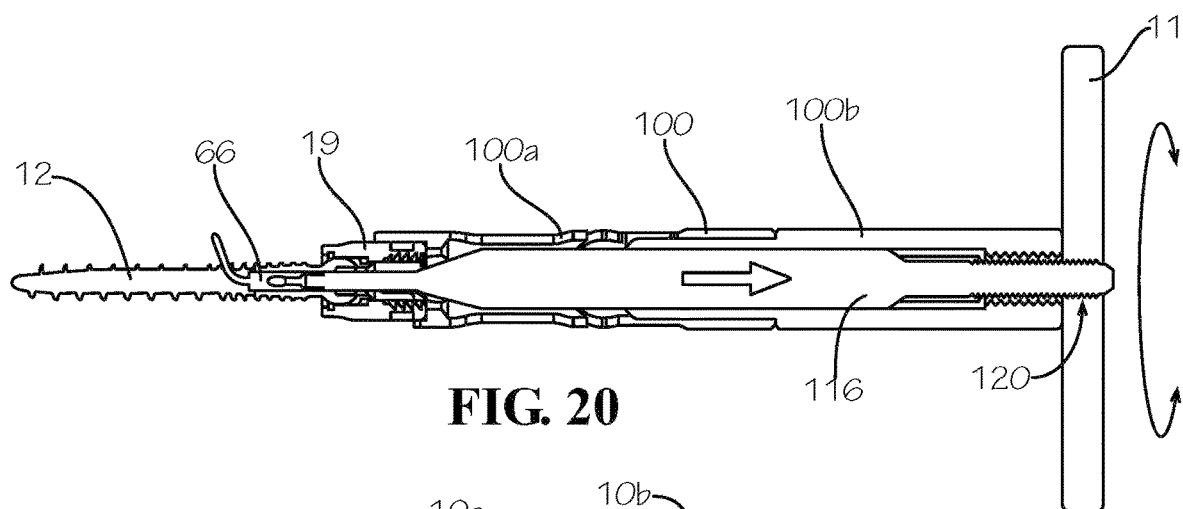
FIG. 20
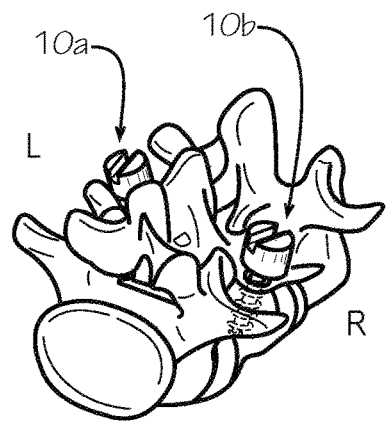
FIG. 21
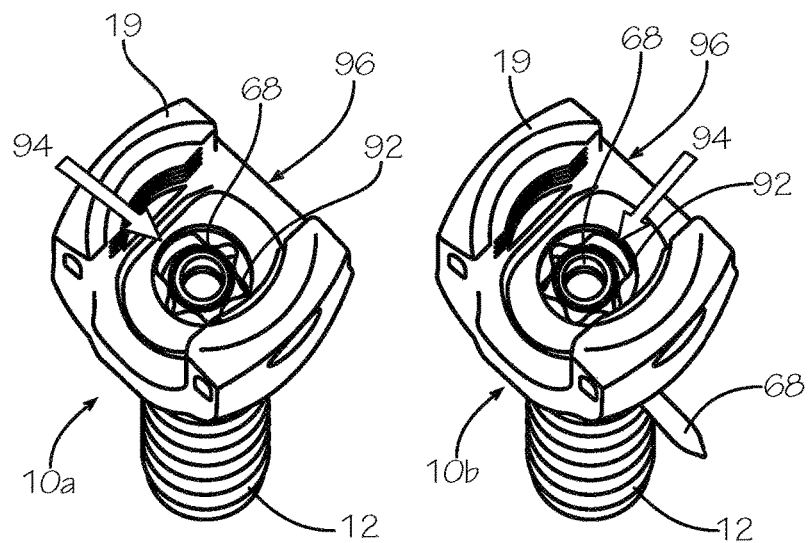
FIG. 21a     FIG. 21b

BONE FIXATION SCREW WITH DEPLOYABLE ANCHORS

CROSS-REFERENCES TO RELATED APPLICATIONS

This application is a non-provisional of U.S. Patent Application Ser. No. 62/418,533 filed Nov. 7, 2016 entitled TRANSCORTICAL FIXATION PEDICLE SCREW WITH DEPLOYABLE ANCHORS, which is herein incorporated by reference in its entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to bone fixation devices, and more particularly, to improved bone screw constructs.

The prevalence of degenerative bone conditions requiring surgery and screw and rod support structures has steadily increased over the past four decades. Degenerative spinal conditions are becoming particularly prevalent in recent years, with pedicle screw and rod systems having become the most common treatment to obtain thoracolumbar spinal fusion worldwide. The incidence of spinal surgery and other bone fixation procedures in the United States is expected to further increase even more rapidly as more and more members of the "baby boomer" generation reach age 65. However, the rapidly growing aging population presents a challenge to effective and durable screw fixation because the increased rigidity of older bones increases pull-out stress on bone screw constructs, while the poor bone quality of osteopenic and osteoporotic patients decreases the ability of screw structures to maintain firm purchase with such bones. As a result, screw loosening and bone fusion failure occur at nearly ten times the normal rate in elderly and osteoporotic patients, representing a significant health detriment to the aging bone fusion population at large and a financial burden to the U.S. healthcare system.

Currently, the most commonly practiced solutions to poor bone screw purchase in osteoporotic and rigid aging patients are: 1) bone cement augmentation of the bone either prior to bone screw insertion or through a cannulated bone screw once placed; 2) increased bone screw thread count and unique thread designs to better purchase the screw within the desired bone walls; 3) expansion of the distal end of the bone screw to disallow unidirectional complete screw pull-out; 4) use of less rigid or dynamic rods to decrease pull-out forces on the screw-bone interface; and 5) more aggressive external bracing of the patient's body in the post-operative period. Despite these advancements, bone screw fixation failures and pseudo arthrosis remain a common complication in the treatment of elderly and osteoporotic patients.

In particular, current pedicle screw systems aim to use outer screw threads to partially cut into the inner cortical bone rim of the pedicle while the center of the pedicle screw sits in the very soft cancellous bone center. This concept relies on the surgeon to place the ideal pedicle screw diameter to best fit the pedicle diameter to maximize the fixation force between the screw thread-inner cortical bone interface. This remains a sub-optimal solution because the inner cortical bone wall-screw thread interface often provides sub-optimal screw fixation that may allow bidirectional screw movement within the bone when stressed several thousand times per month in the average mobile patient. Even when optimal screw thread-inner cortical bone rim purchase is achieved at surgery, the osteoporotic inner cortical rim is often not rigid or durable enough to maintain the desired thread-bone fixation.

What is needed, then, are improved bone screw systems that help provide increased multi-directional pull-out strength and durability so as to better purchase and fixate various bones within a patient.

BRIEF SUMMARY OF THE INVENTION

One aspect of the present disclosure is a screw device for implantation into a bone of a patient. The screw device includes a screw body having an outer surface. A plurality of outer screw threads extends around the outer surface of the screw body. A plurality of apertures is defined through the outer surface. A plurality of anchors can extend out of corresponding apertures in the screw body. The anchors can be inserted into a patient's bone to further fixate and purchase the bone screw within the patient's bone. The screw body can include an inner cavity in some embodiments. The plurality of apertures can each be open to the inner cavity. The anchors can extend out of corresponding apertures from the inner cavity.

Another aspect of the present disclosure is a screw device for implantation into a bone of a patient including a screw body having an outer surface and an inner cavity. A plurality of outer screw threads can extend around the outer surface of the screw body. A first aperture can be defined in the outer surface of the screw body, the first aperture open to the inner cavity. A second aperture can be defined in the outer surface of the screw body, the second aperture open to the inner cavity. A first anchor pin can be inserted through the inner cavity and be extended out of the first aperture. A second anchor pin can be inserted through the inner cavity and extended through the first anchor pin and out of the second aperture when the first anchor pin is extended through the first aperture.

In some embodiments, the bone screw of the present disclosure can be used as a transcortical fixation pellicle screw which can allow the pedicle screw to better take advantage of the most rigid and durable bone in the osteoporotic spine: the cortical bone rim of the pellicle. The anchor system of the bone screw can fixate across the inner and outer cortical bone rim of the pedicle and translate multi-direction forces placed on the screw to the full cortical bone wall. The transcortical anchor concept can help take advantage of a more rigid bone in the pellicle's anatomy, moving fixation force demands from the soft cancellous bone of the spine to the more rigid bone available (the trans-cortical bone wall). Anchors can be oriented to deploy away from the spinal canal and nerve roots, such that the pellicle screws can be placed and anchors deployed immediately following bone cement augmentation to allow even greater fixation while reducing the risk of cement migration onto nerve elements.

In some embodiments, the bone screw can have two or more anchors to load share multi-directional forces on the bone screw. In other embodiments, the bone screw can have 6 or more anchors. In some embodiments, deploying the bone anchors can be facilitated by connecting and turning a driver, or connecting and injecting fluid hydraulics, on or into the visible proximal end of the pellicle screw after placement.

Numerous other objects, advantages, and features of the present invention will be readily apparent to those of skill in the art upon a review of the following drawings and description of a preferred embodiment.

BRIEF DESCRIPTION OF THE SEVERAL VIEWS OF THE DRAWINGS

FIG. 20 is a cross sectional view of a removal shaft connected to a first anchor pin of the bone screw of FIG. 19 for removal of the first anchor pin.

FIG. 21 is a perspective view of multiple bone screws of FIG. 5 being used as pedicle screws and installed in the left and right pedicles of the patient.

FIG. 21a is a top perspective view of a pedicle screw for installation in a left side pedicle of a patient.

FIG. 21b is a top perspective view of a pedicle screw for installation in a right side pedicle of a patient.

DETAILED DESCRIPTION OF THE INVENTION

Figure 1A:
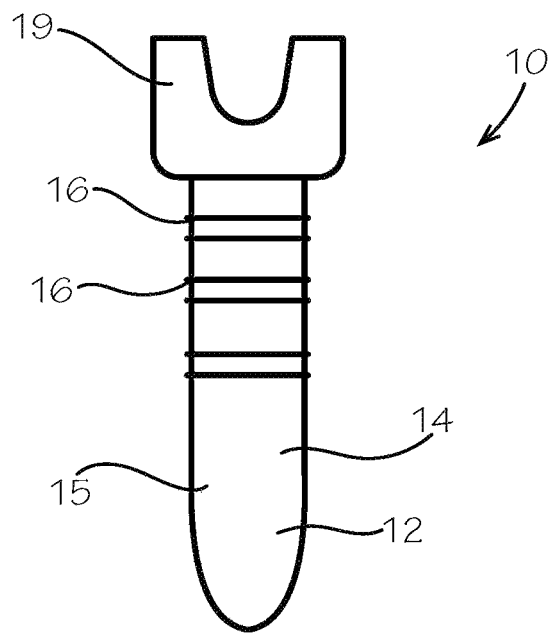
FIG. 1a is a front elevation view of an embodiment of a bone screw with deployable anchors, the anchors being in a retracted position.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

As described herein, an upright position is considered to be the position of apparatus components while in proper operation or in a natural resting position as described herein. Vertical, horizontal, above, below, side, top, bottom, and other orientation terms are described with respect to this upright position during operation unless otherwise specified. The term "when" is used to specify orientation for relative positions of components, not as a temporal limitation of the claims or apparatus described and claimed herein unless otherwise specified. The term "lateral" denotes a side to side direction when facing the "front" of an object.

The phrase "in one embodiment," as used herein, does not necessarily refer to the same embodiment, although it may. Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

This written description uses examples to disclose the invention and also to enable any person skilled in the art to practice the invention, including making and using devices or systems and performing any incorporated methods. The patentable scope of the invention is defined by the claims, and may include other examples that occur to those of skill in the art. Such other examples are intended to be within the scope of the claims if they have structural elements that do not differ from the literal language of the claims, or if they include equivalent structural elements with insubstantial differences from the literal language of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the apparatuses and/or methods disclosed and claimed herein may be made and/or executed without undue experimentation in light of the present disclosure. While the apparatuses and methods of this invention have been described in terms of the embodiments included herein, it will be apparent to those of ordinary skill in the art that variations may be applied to the apparatuses and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims An embodiment of a bone screw 10 is shown in FIG. 1a. The bone screw 10 can include a screw body 12 having an outer surface 14 and a plurality of apertures 16 defined in and through the outer surface 14. In some embodiments, the screw body 12 can include external threads extending around the outer surface 14 of the screw body 12 to facilitate insertion of the bone screw 10 into a bone of a patient. In some embodiments, the screw body 12 can include a sidewall 15 and an inner cavity 17, and the plurality of apertures 16 can be defined in or extend through the sidewall 15 and be open to the inner cavity 17. In other embodiments, the apertures 16 can extend into one or more channels or passages defined through the screw body 12.

Figure 1B:
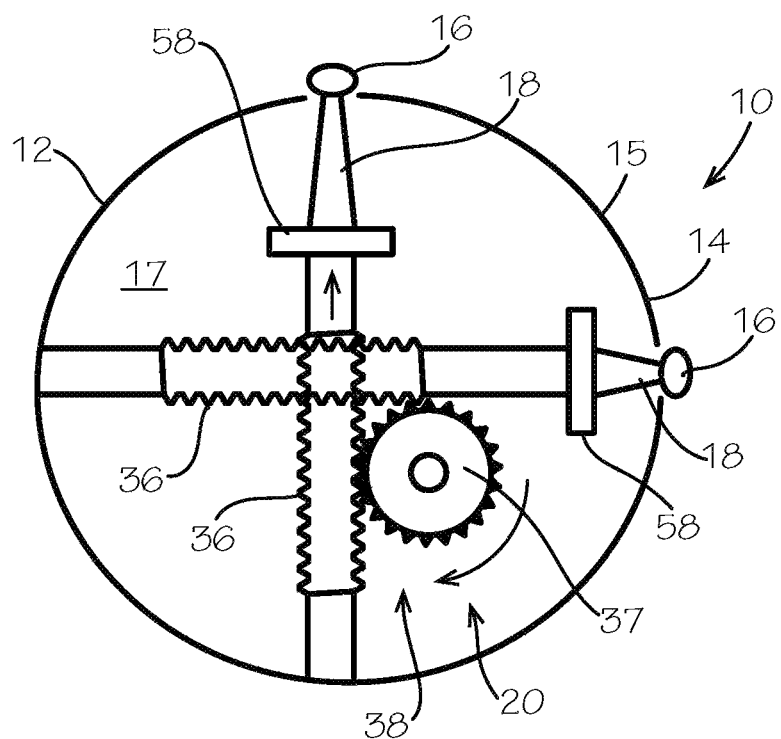
FIG. 1b is a cross sectional view of the bone screw of FIG. 1a with the anchors in a retracted position.

A cross-sectional view of the bone screw 10 of FIG. 1a is shown in FIG. 1b. The bone screw 10 can include a plurality of deployable anchors 18 disposed in the screw body 12. The plurality of anchors 18 can each be extendable out of a corresponding aperture 16 in the outer surface 14 of the screw body 12. In some embodiments, each of the anchors 18 in the plurality of anchors 18 can be aligned with a corresponding aperture 16 in the outer surface 14 of the screw body 12. In those embodiments including one or more channels within the screw body 12, the anchors 16 can be positioned in corresponding channels of the screw body 12. The bone screw 10 in some embodiments can include an actuator 20 coupled to the plurality of anchors 18. The actuator 20 can be operable to move the plurality of anchors 18 between a retracted position, as shown in FIG. 1b, and a deployed position, as shown in FIG. 1d. In the retracted position, the plurality of anchors 18 are positioned within the sidewalls 15 and the outer surface 14 of the screw body 12, or extend minimally beyond the sidewalls 15 of the screw body 12. As such, in the retracted position, distal ends of the anchors 18 generally do not extend, or extend minimally, outward from the outer body surface 14. In the deployed position, each anchor 18 of the plurality of anchors extends through the corresponding aperture 16 in the outer body surface 14 such that anchors 18 can extend outward from the outer body surface 14 of the screw body 12 to able to engage a bone or a bone wall of the patient.

As such, the screw body 12 can be inserted or driven into a patient's bone during surgery with the anchors 18 in a retracted position, the threads on the screw body 10 helping fix or purchase the screw body 12 within the bone. Once the screw body 12 is in a desirable position within the bone, the anchors 18 can be deployed to drive the anchors 18 into the bone to provide further purchase and fixation of the screw body 12 within the bone.

In some embodiments, the bone screw 10 can be used as a pedicle screw 10 which can be inserted into the pedicle of a patient's spine. The screw body 12 can be inserted into the cancellous bone center of the pedicle with the anchors 18 in the retracted position. The threads on the screw can engage the trans-cortical bone wall of the pedicle. Once the pedicle screw 10 is in the proper position within the pedicle, the actuator 20 can be operable to move the plurality of anchors 18 from the retracted position shown in FIG. 1b to the deployed position shown in FIG. 1d. As the plurality of anchors 18 moves to the deployed position, the anchors 18 can extend outward from the outer body surface 14 and be fixated or purchased in the trans-cortical bone wall of the pedicle. The anchors 18 once fixated to the cortical bone wall of the pedicle can help translate multi directional forces placed on the pedicle screw 10 to the cortical bone wall of the pedicle. The anchors 18 can help the pedicle screw 10 take advantage of the rigid bone of the cortical bone wall, which can move the fixation force demands on the pedicle screw 10 from the soft cancellous bone, as in current solutions, to one of the more rigid bones available in the pedicle. Such an embodiment can help provide structural strength and rigidity to the pedicle screw 10 and help prevent the pedicle screw 10 from dislodging from the pedicle once the pedicle screw 10 is implanted.

Figure 1C:
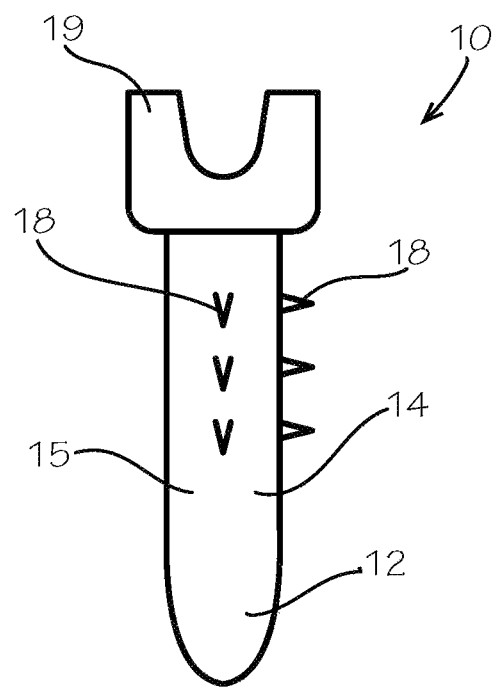
FIG. 1c is a front elevation view of the bone screw of FIG. 1a with the deployable anchors in a deployed position.
Figure 1D:
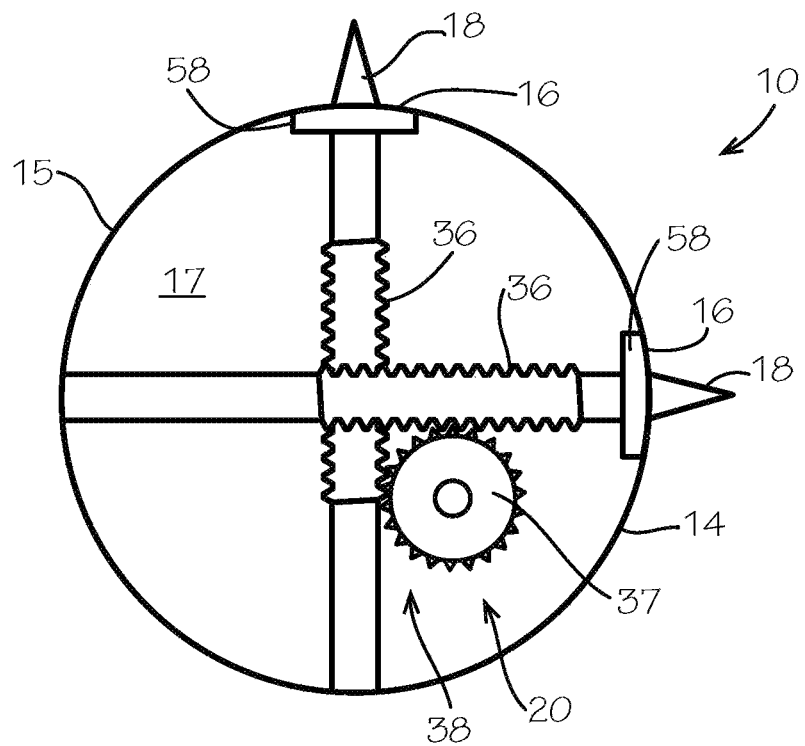
FIG. 1d is a cross sectional view of the bone screw of FIG. 1a with the anchors in the deployed position.

As can be seen from FIGS. 1c and 1d, the plurality of anchors 18 can be oriented such that the anchors 18 are deployed in varying radial directions from the screw body 12. In some embodiments, the plurality of anchors 18 can also include multiple rows of anchors, each row extending in a direction parallel to the longitudinal axis 24 of the screw body 12, as shown in FIG. 1c. The anchors 18 can thus engage and be fixated to the desired bone wall at varying radial and longitudinal locations. The fixation forces on the pedicle screw 10 can therefore be translated by the anchors 18 to varying radial and longitudinal locations of the desired bone which can help provide a more stable and reliable purchase of the bone screw 10 in the desired bone. In some embodiments, the bone screw 10 can have six anchors, as shown in FIG. 1c. However, a varying number of anchors 18 can be used in different embodiments. In some embodiments, the bone screw 10 can have three rows of anchors while varying numbers of rows of anchors can be used in different embodiments. Additional anchors 18 and radial and longitudinal positions for such anchors 18 can allow the fixation forces to be spread across a larger number of anchors 18, which can help reduce the fixation forces on any one anchor 18. Reducing the fixation forces on any one anchor 18 can help increase the reliability and longevity of the bone screw 10 purchase as the risk of fracture or failure of the anchors 18 can be reduced. Additional anchors 18 at varying radial and longitudinal positions can also provide additional fixation points between the bone screw 10 and the desired bone across a larger surface area of the bone, thereby helping to reduce stresses applied at any single location on the desired bone of the patient.

Figure 1E:
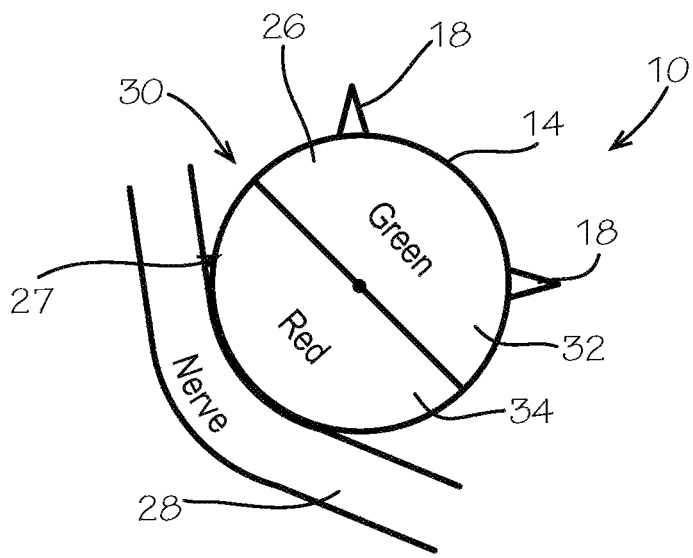
FIG. 1e is a coronal view of an implanted bone screw of FIG. 1c showing a top view of the bone screw being utilized as a pellicle screw.
Figure 1F:
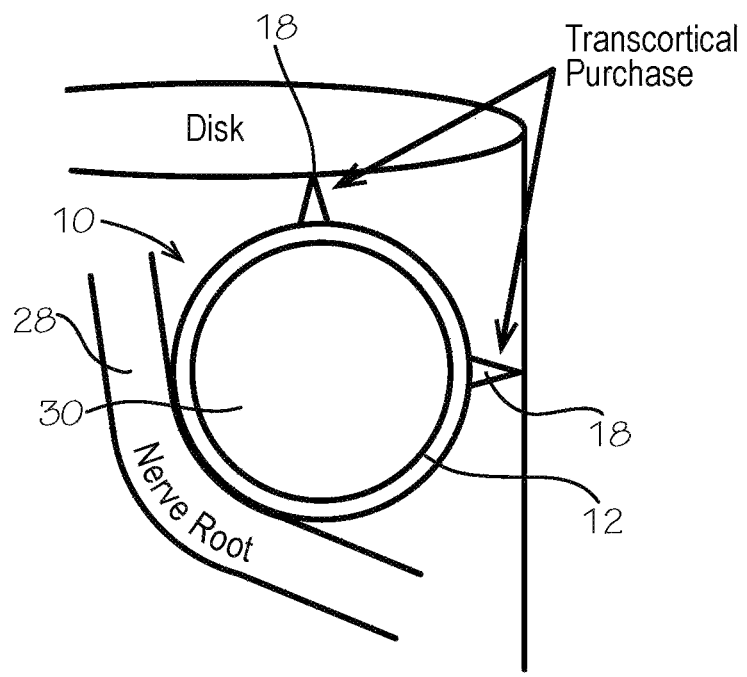
FIG. 1f is another coronal view of an implanted bone screw of FIG. 1c showing purchase of the bone screw in the cortical bone wall of the pellicle.

Turning to FIGS. 1e and 1f, a coronal view is shown of the bone screw 10 of FIG. 1a implanted into a pedicle of a patient, the bone screw 10 utilized as a pedicle screw. A top view of the pedicle screw 10 is seen in FIG. 1e. In some embodiments, the anchors 18 can protrude from only a first half 26 of outer surface 14 of the screw body 12. As such, when the pedicle screw 10 is implanted into a pedicle, the first half 26 of outer surface 14 can be oriented by the surgeon away from a nerve root 28 positioned in close proximity to the pedicle, while a second half 27 of the outer surface 14 can be oriented toward the nerve root 28. In some embodiments, the top 30 of the pedicle screw 10 can be color coded to denote the half of the outer surface 14 from which the anchors 18 will be deployed. For instance, a first top half 32 of the top 30 of the pedicle screw 10 can be in one color, the first top half 32 positioned above the first half 26 of the outer surface 14. A second top half 34 of the top 30 of the pedicle screw 10 positioned above a second half 27 of the outer surface 14 can be in a different color. As such, when a surgeon is implanting the screw into the pedicle of a patient, the surgeon can look at the proximal top 30 of the pedicle screw 10 and properly orient the screw 10 such that the anchors 18 when deployed will extend away from the nerve root 28. Having the anchors 18 extend away from the nerve root 28 can help prevent damage to the nerve root 28 from the anchors 18. Additionally, when cementation is used to additionally fixate the pedicle screw 10 to the pedicle, having the anchors 18 extending away from the nerve root 28 will help reduce the risk of cement migrating to the nerve root 28, which can potentially cause damage to the nerve root 28.

In some embodiments, as shown in FIGS. 1b and 1d, the actuator 20 can be a drive gear system 38. Each anchor 18 can include a linear gear 36. In some embodiments, the drive gear system 38 can be a single driving gear 37 that is meshed with all of the linear gears 36 on the plurality of anchors 18. In other embodiments, the drive gear system 38 can include multiple drive gears 37, each drive gear meshed with one or more linear gears 36 of the plurality of anchors 18. As such, the drive gear system 38 can be rotated by a driver or drive shaft to translate the anchors 18 via the linear gears 36 between the retracted position and the deployed position. In FIGS. 1b and 1d, the drive gear 37 can be rotated in a clockwise direction to move the anchors 18 to the deployed position, and the drive gear 37 can subsequently be rotated in a counter clockwise direction to return the anchors 18 to the retracted position. In other embodiments, the drive gear 37 can be oriented within the inner cavity 17 such that the driving directions for drive gear 37 can be reversed.

Figure 2A:
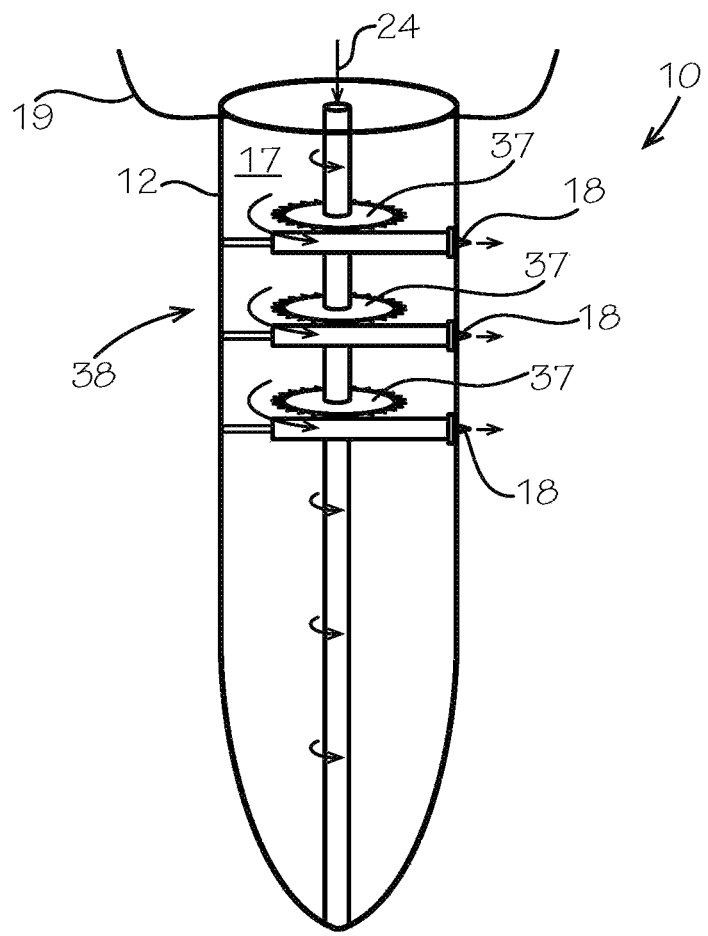
FIG. 2a is a cutaway view of a second embodiment of a bone screw having deployable anchors and a central drive gear system.
Figure 2B:
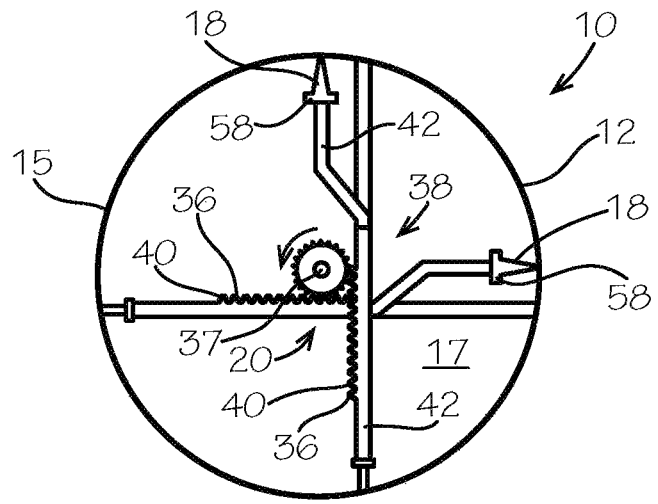
FIG. 2b is a cross sectional view of the bone screw of FIG. 2a with the anchors in a retracted position.
Figure 2C:
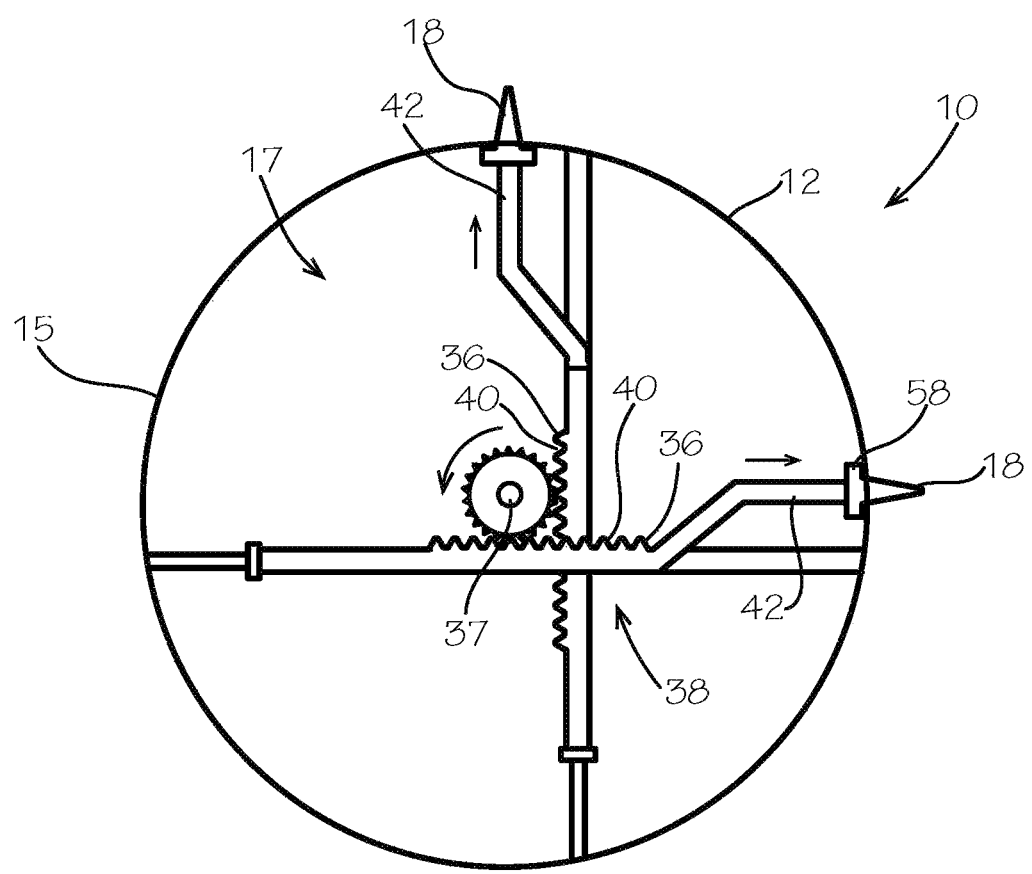
FIG. 2c is a cross sectional view of the bone screw of FIG. 2a with the anchors in a deployed position.

In some embodiments, as shown in FIGS. 1b and 1d, the drive gear 37 can be positioned eccentrically with respect to the screw body 12. As such, the anchors 18 can be substantially linear and traverse the longitudinal axis of the screw body 12. In other embodiments, as shown in FIGS. 2a-2c, the drive gear 37 can be positioned concentrically with the screw body 12 and coaxially with the longitudinal axis 24 of the screw body 12. In such embodiments, the anchors 18 can have a bent shape such that the anchors 18 can extend around the drive gear 37 and still extend radially outward from the screw body 12. The anchors 18 in FIG. 2b can have a meshing portion 40 including a linear gear 36 meshed with the drive gear 37, and an extension portion 42 extending in a radially outward direction. In still other embodiments having a concentric drive gear 37, the anchors 18 can be substantially linear and oriented to extend in a direction that is angularly offset from a radially outward direction.

Figure 3A:
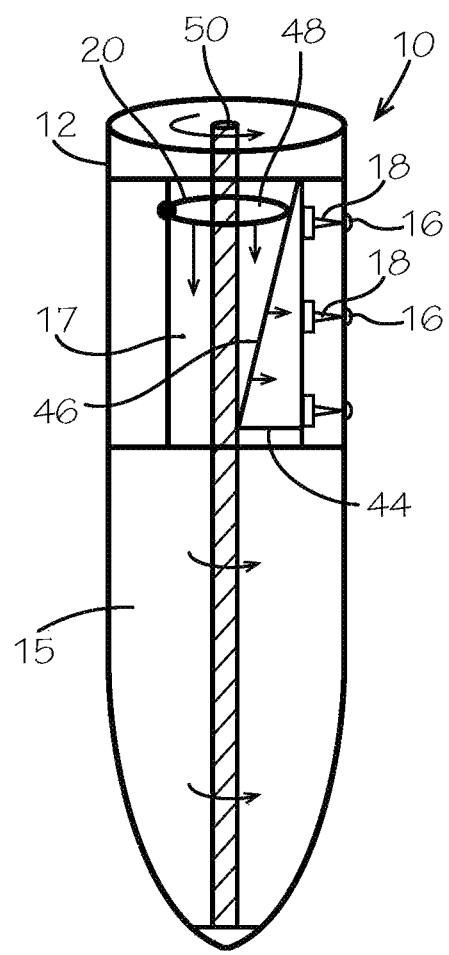
FIG. 3a is a cutaway view of a third embodiment of a bone screw having deployable anchors with the anchors in a retracted position, the bone screw including a plunger system to actuate the deployment of the anchors.
Figure 3B:
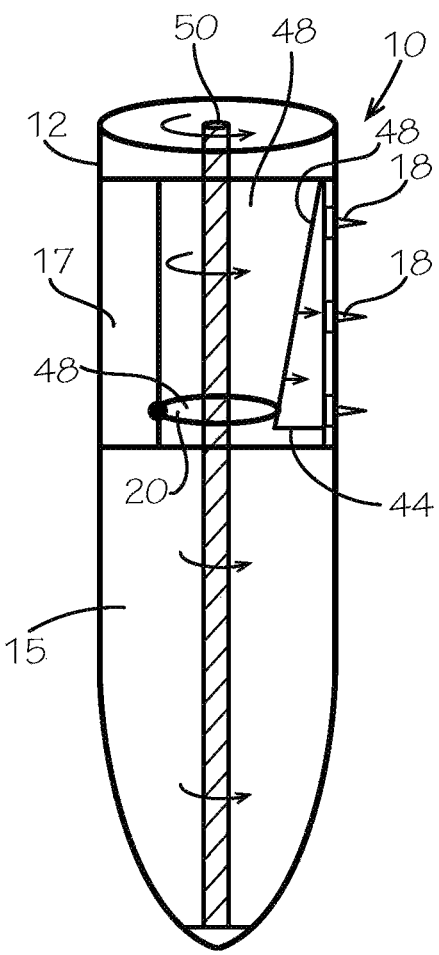
FIG. 3b is a cutaway view of the bone screw of FIG. 3a with the anchors in a deployed position.

Another embodiment of a bone screw 10 is shown in FIGS. 3a-3b. In some embodiments, the anchors 18 can be connected to one or more plates 44, each plate 44 having an angled interior surface 46. The plates 44 and the anchors 18 can be movable within the screw body 12 between a retracted position and a deployed position. The actuator 20 can be a movable plunger 48 on a threaded shaft 50. As the threaded shaft 50 is rotated the plunger 48 can move up and down to effectively move the plate 44 and the anchors 18 between the retracted position and the deployed position. The plunger 48 is shown in an upper position in FIG. 3a, with the plate 44 in the retracted position. As the threaded shaft 50 is rotated and the plunger 48 moves to the lower position shown in FIG. 3b, the plunger 48 can exert an outward force on the interior angled surface 46 of the plate 44 and effectively move the plate 44 and the anchors 18 in an outward direction to engage the anchors 18 with the bone wall of the patient's. To remove the bone screw 10, the threaded shaft 50 can be rotated such that the plunger 48 returns to the upper position and the plate 44 can be allowed to return to the retracted position such that the anchors 18 disengage from the bone of the patient. In some embodiments, the plates 44 can be biased toward the retracted position, for instance via a spring, to return the plates 44 and the anchors 18 to the retracted position as the plunger 48 moves to the raised position.

Figure 4A:
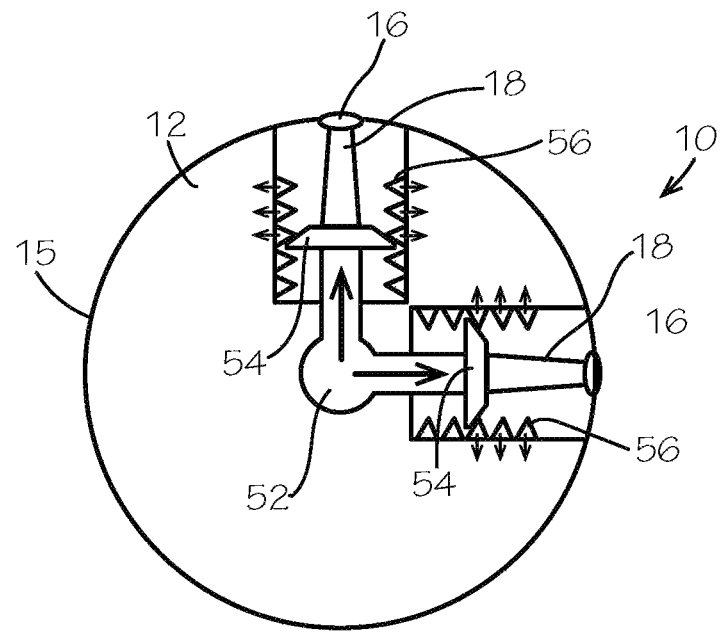
FIG. 4a is a cross sectional view of a fourth embodiment of a bone screw including hydraulic actuation of the deployable anchors, the anchors being in a retracted position.
Figure 4B:
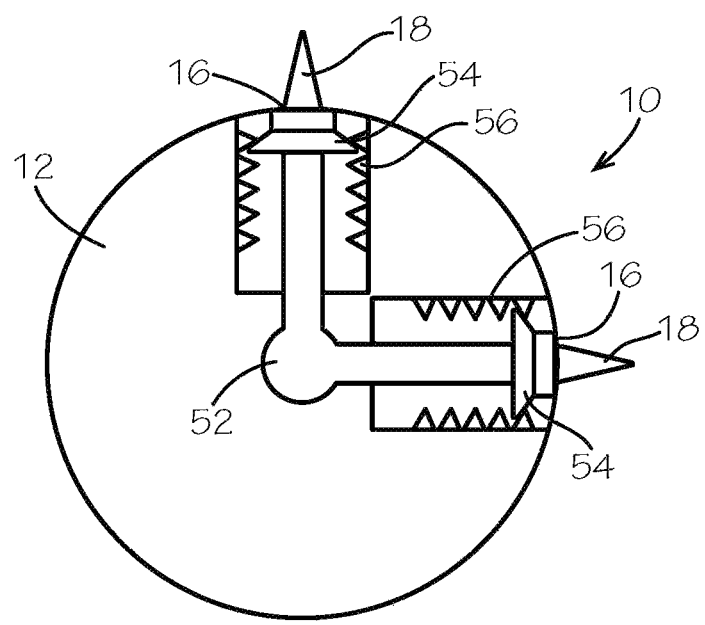
FIG. 4b is a cross sectional view of the bone screw of FIG. 4a with the anchors in a deployed position.
Figure 4C:
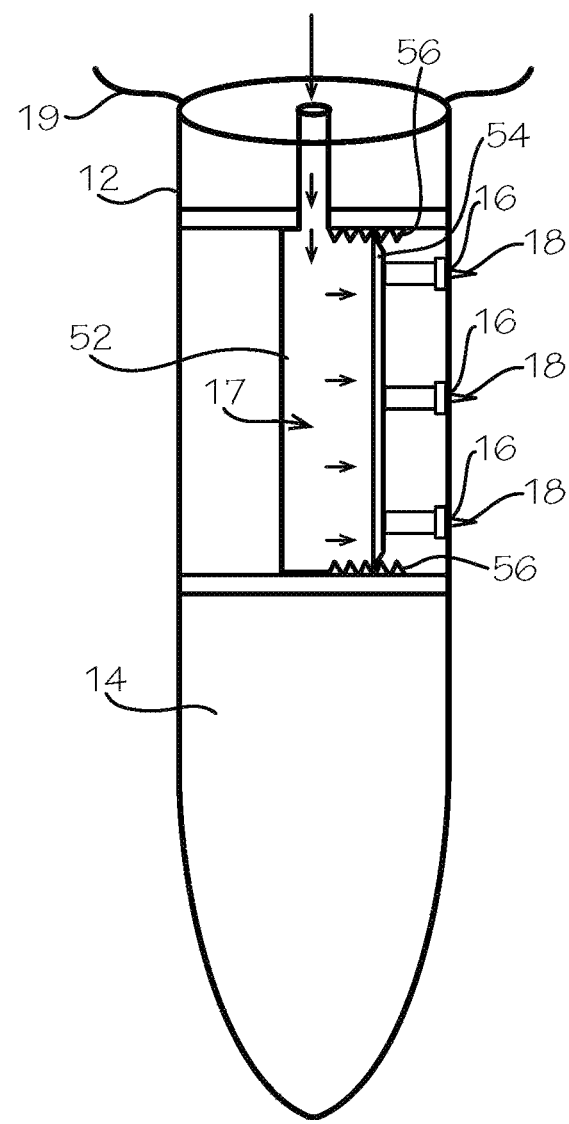
FIG. 4c is a cutaway view of the bone screw of FIG. 4b.

Another embodiment of a bone screw 10 is shown in FIGS. 4a-4c. In some embodiments, the screw body 12 can include a hydraulic chamber 52. The anchors 18 can be fixed to one or more flat plates 54 positioned within the hydraulic chamber 52. The flat plates 54 and the anchors 18 can be movable within the hydraulic chamber 52 between a retracted position and a deployed position. With the hydraulic chamber 52 unpressurized, the flat plates 54 can be oriented in the retracted position. Once the bone screw 10 is in position within a desired bone of a patient, a hydraulic fluid can be pumped into the hydraulic chamber 52, as shown in FIGS. 4b and 4c, effectively forcing the flat plates 54 in an outward direction to engage the anchors 18 with the desired bone. The hydraulic fluid could subsequently be removed to allow the anchor pins 18 to return to a retracted position. In some embodiments, the anchors 18 could again be biased, for instance via a spring, to return to the retracted position as the hydraulic fluid and hydraulic pressure is removed from the hydraulic chamber 52. In some embodiments, a pneumatic system could be utilized for the actuator 20, the pneumatic system having a pneumatic chamber which can receive a pressurized gas to force the flat plates 54 outward to engage the anchors 18 with the desired bone.

In some embodiments, as shown in FIGS. 4a-4c, the screw body 12 can include one or more mechanical hinged stops 56. The hinged stops 56 can be configured to pivot as the anchors 18 or the plates 44 move from the retracted position to the deployed position, thus allowing the anchors 18 to engage the bone wall. However, the hinged stops 56 can help prevent the anchors 18 from returning to the retracted position or dislodging from the bone wall under normal physiological stresses on the bone screw 10. As such, the mechanical hinges 56 can help prevent the bone screw 10 from unintentionally dislodging due to natural movement of the patient over time. However, the mechanical hinges 56 can be designed to break away when supra-physiological forces are applied to the bone screw 10, for instance by a surgeon during removal of the bone screw 10 from the patient. As such, when it is desirable to remove the bone screw 10 from a patient's bone, a reverse force from the actuator 20 can cause the mechanical hinges 56 to break away such that the anchors 18 can be dislodged from the bone and returned to the retracted position so that the bone screw 10 can be removed from the patient's bone.

In other embodiments, the stops 56 can be movable into the screw body 12 and biased toward an extended position. As the anchors 18 move from the retracted position to the extended position, the anchors 18 move the stops 56 into the screw body 12. Once the anchors 18 pass the stops 56, the stops 56 can be returned to the extended position. The stops 56 can be designed to prevent the return of the anchors 18 to the retracted position under normal physiological stresses, but the stops 56 can break away when supra-physiological forces are applied to the anchors 18.

For each of the embodiments previously mentioned, the anchors 18 can be configured to meet an inner surface or inner wall of the screw body 12, effectively stopping the outward movement of the anchors 18. In FIGS. 1a-2c, the anchors 18 can include a base 58 which can abut against the inner surface of the screw body 12 to stop the radial movement of the anchors 18. In FIGS. 3a-3b, the angled plates 44 can abut against the inner surface of the screw body 12 to stop the outward movement of the anchors 18. In FIGS. 4a-4c, the flat plates 54 can abut against the inner surface of the screw body 12 to stop the outward movement of the anchors 18. As the bases 58, plates 44, or flat plates 58 hit the inner surface of the screw body 12, a threshold force is achieved on the actuator 20 which can signal or indicate full deployment. In the gear drive systems and plunger systems, an increased mechanical torque on the driver and gear or plunger system from the inner surface of the screw body 12 will indicate full deployment. In the hydraulic or pneumatic systems, a pressure gauge can be used to indicate when full deployment has occurred. When the anchors 18 are at full deployment, pumping additional fluid or gas into the hydraulic or pneumatic chambers respectively will increase the pressure inside the hydraulic or pneumatic chambers to above a predetermined threshold amount. The pressure gauge can be used to determine when the pressure has increased above the threshold amount, signaling full deployment.

Another embodiment of a bone screw 10 of the present disclosure is shown in FIGS. 5-20. The screw body 12 can include an outer surface 14 and an inner cavity 17. A plurality of outer screw threads 60 can extend around the outer surface 14 of the screw body 12. A first aperture 62 can be defined in the outer surface 14 of the screw body 12, the first aperture 62 being open to the inner cavity 17. A second aperture 64 can be defined in the outer surface 14 of the screw body 14, the second aperture 64 being open to the inner cavity 17. A first anchor pin 66 can be extendable out of the first aperture 62 from the inner cavity 17, and a second anchor pin 68 can be extendable out of the second aperture 64 from the inner cavity 17. The first and second anchor pins 66 and 68 can be extendable beyond the outer screw threads 60 on the screw body 12, such that multiple anchor pins 66 and 68 can be extended out of the screw body 12 via corresponding apertures 62 and 64 beyond the outer screw threads 60 to help purchase and fixate the bone screw 10 within the bone of a patient.

Figure 5:
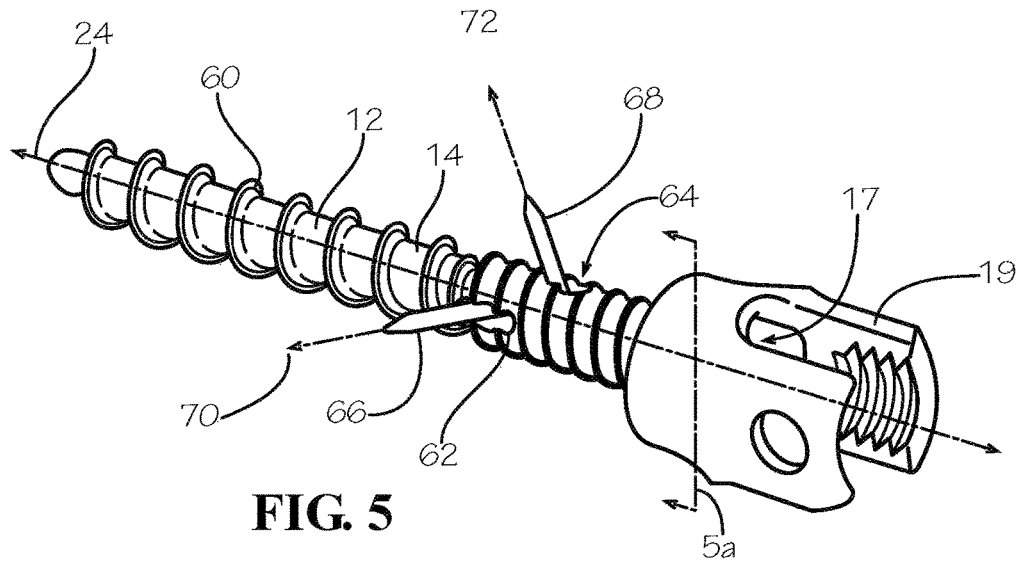
FIG. 5 is a perspective view of another embodiment of a bone screw having anchors that are inserted through an inner cavity in a screw body and out of corresponding apertures in the screw body.
Figure 5A:
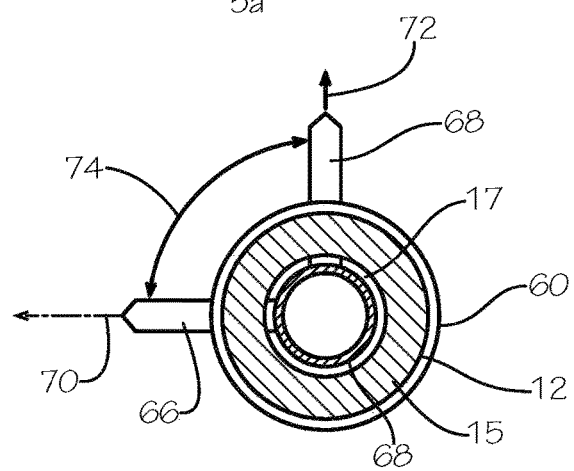
FIG. 5a is a cross sectional view of the bone screw of FIG. 5.

As can be seen in FIG. 5, in some embodiments, the first anchor pin 66 can extend from the screw body 12 generally in a first direction 70, and the second anchor pin 68 can extend from the screw body 12 in a second direction 72. First and second directions 70 and 72 can be oriented transverse to the longitudinal axis 24 of the screw body 12. In some embodiments, the anchor pins 66 and 68 can extend in respective directions 70 and 72 that are oriented perpendicular to a longitudinal axis 24 of the screw body 12, while in other embodiments, the anchor pins 66 and 68 can extend from the screw body 12 at an acute angle with the longitudinal axis 24 of the screw body 12. In some embodiments, the first and second directions 70 and 72 can be oriented radially perpendicular to one another, as shown in FIGS. 5 and 5a, or the radial portions of the first and second extension directions 70 and 72 can be oriented perpendicular to one another. A radial portion of an extension direction is the portion of the extension direction extending in a radial direction from the longitudinal axis 24. The first and second extension directions 70 and 72 can form a radial angle 74 that is about 90 degrees in some embodiments. In other embodiments, the radial angle 74 between the first and second directions 70 and 72 can be between about 45 and about 135 degrees.

Figure 7:
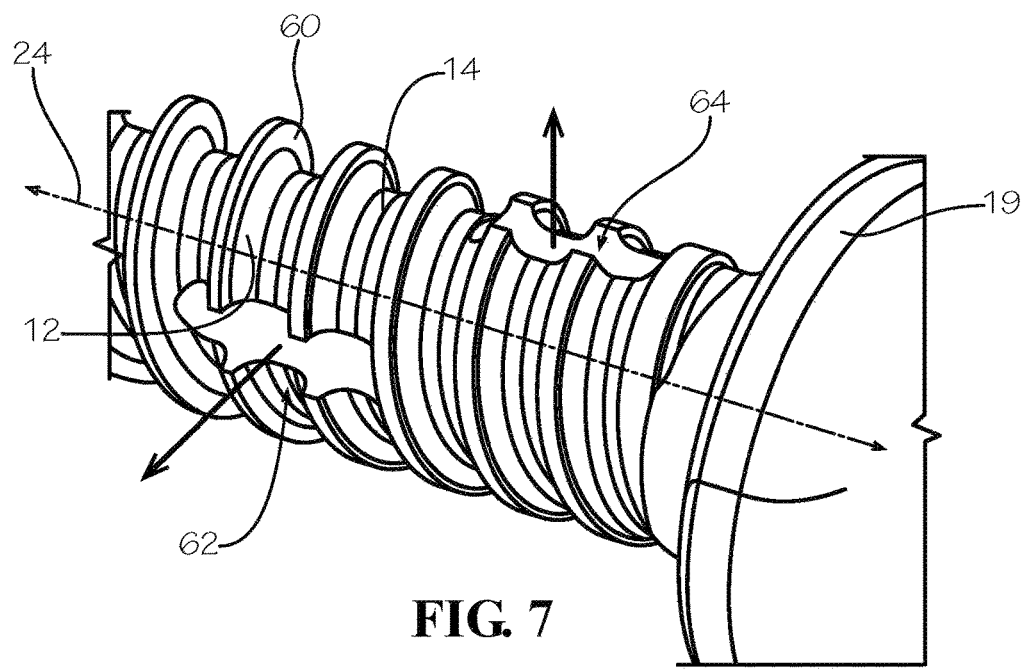
FIG. 7 is a detailed view of the bone screw of FIG. 5 showing the apertures in the screw body.
Figure 8:
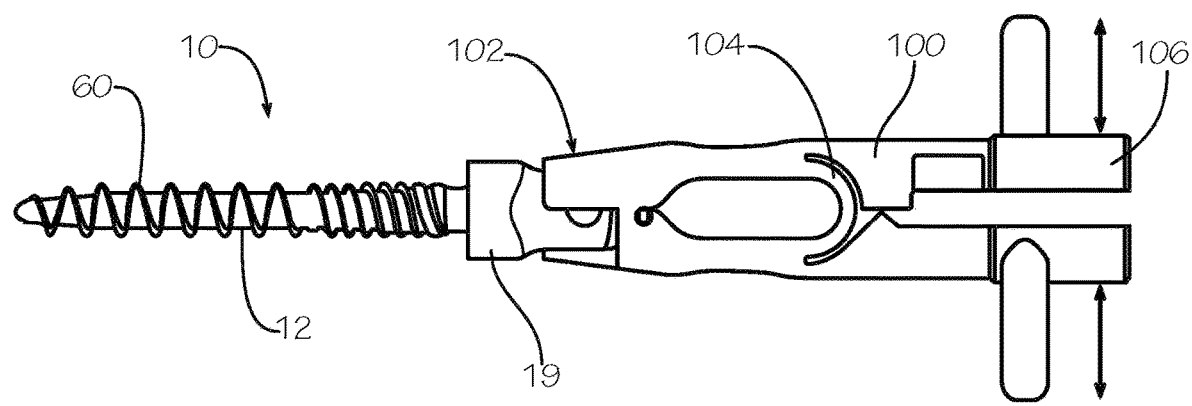
FIG. 8 is a side view of an outer sleeve being secured to the bone screw of FIG. 5.
Figure 9:
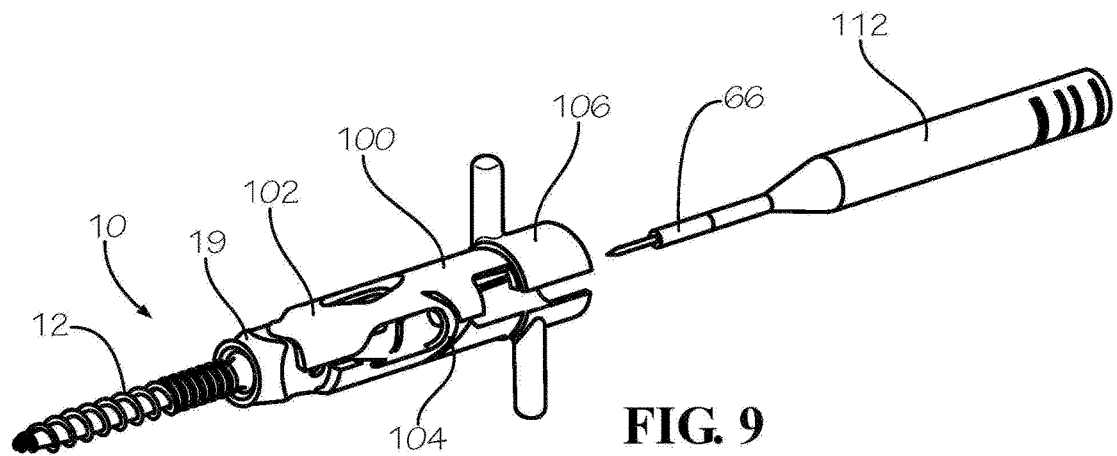
FIG. 9 is a perspective view of a first anchor pin of the bone screw of FIG. 5 connected to an inner shaft and being inserted through an outer sleeve and into the screw body via the inner shaft.

As can be seen in FIG. 7, the first and second apertures 62 and 64 defined on the screw body 12 can be angularly spaced or offset from each other on the screw body 12 about the longitudinal axis 24 such that as first and second anchor pins extend out of first and second apertures 62 and 64 respectively, the first and second anchor pins can extend into the patient's bone from differing directions. In some embodiments, the first and second apertures 62 and 64 can be angular spaced about the longitudinal axis 24 by an angle of about 90 degrees, such that the first and second extension directions of the first and second anchor pins can be oriented radially perpendicular to one another. In other embodiments, the first and second apertures 62 and 64 can be angular spaced about the longitudinal axis 24 by an angle of between about 45 and 135 degrees.

Figure 6:
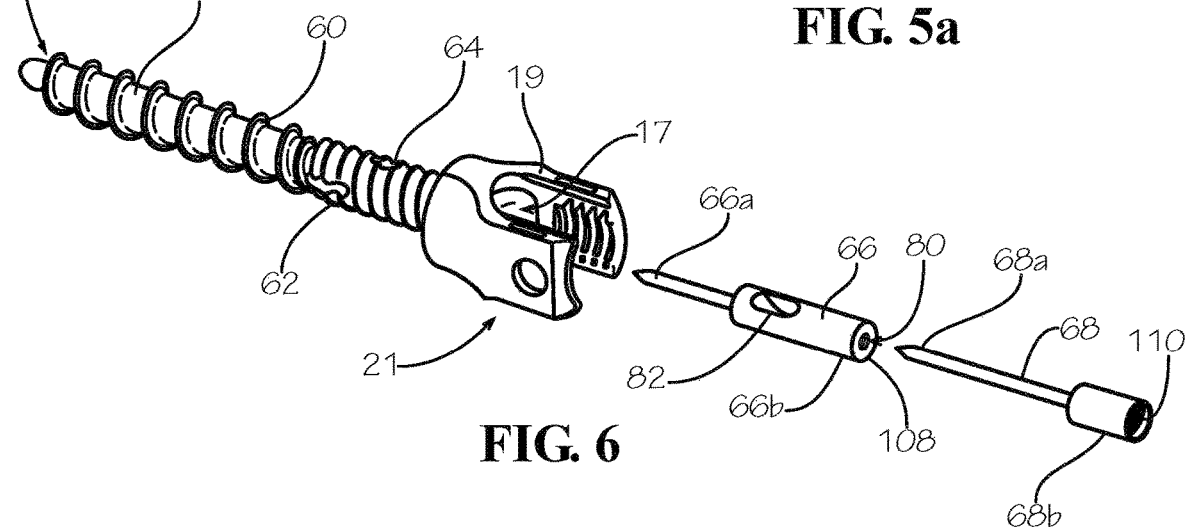
FIG. 6 is an exploded view of the bone screw of FIG. 5.
Figure 10:
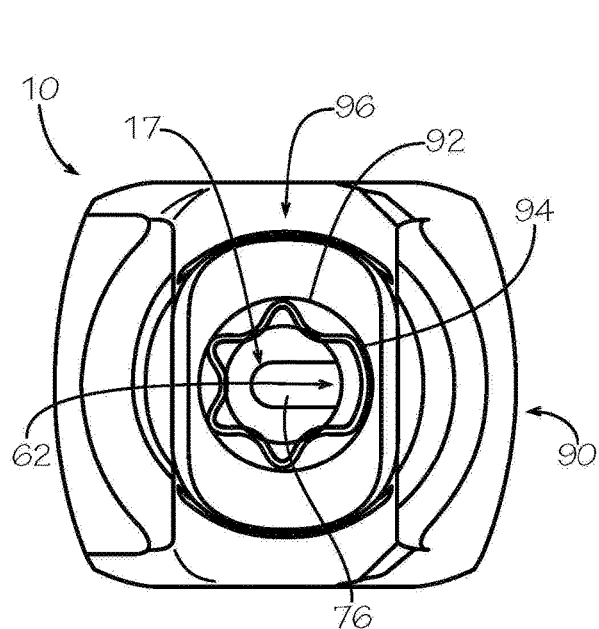
FIG. 10 is a top view of a screw head of the bone screw of FIG. 5.
Figure 11:
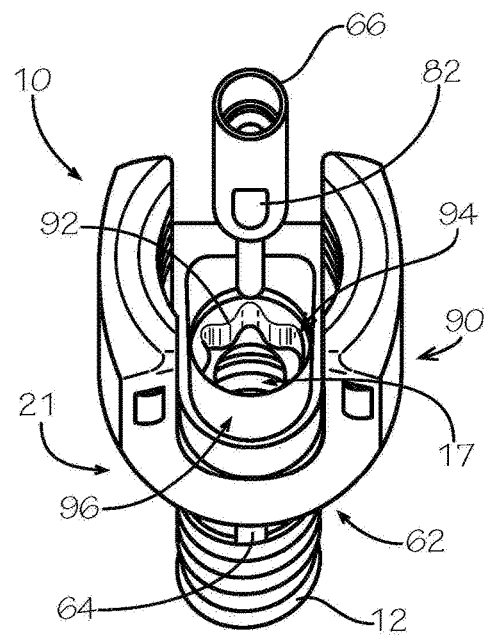
FIG. 11 is a top perspective view of a first anchor pin of the bone screw of FIG. 5 being inserted in the inner cavity of the screw body.

As shown in FIGS. 6 and 10-11, the inner cavity 17 can be defined in the screw body 12 and can be accessible from a proximal end 21 of the screw body 12. In some embodiments, the bone screw 10 can include a screw head 19 positioned on the proximal end 21 of the screw body 12, a distal end 23 of the screw body 12 being pointed, the distal end 23 configured to be inserted into a patient's bone. The inner cavity 17 can also be accessible through the screw head 19. Once the screw body 12 is driven into a patient's desired bone, the first and second anchor pins 66 and 68 can be inserted individually into the inner cavity 17 and forced through the first and second apertures 62 and 64, respectively, to insert the anchor pins 66 and 68 into the patient's bone and further fixate and purchase the bone screw 10 into the patient's bone. In some embodiments, the anchors 66 and 68 can help the bone screw 10 withstand pullout forces greater than or equal to 1000 Newtons. In some embodiments, the anchors 66 and 68 can help the bone screw 10 withstand pullout stresses greater than or equal to 1300 Newtons.

Figure 14:
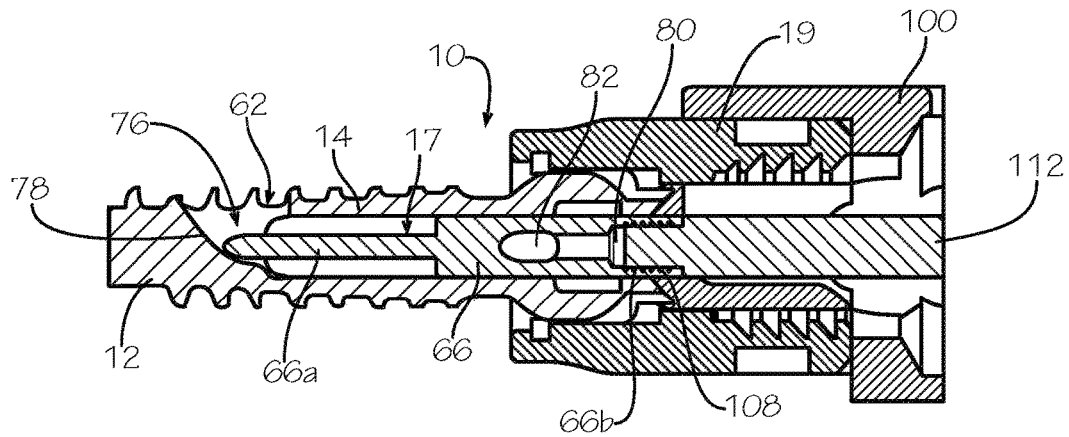
FIG. 14 is a cross sectional view of the bone screw of FIG. 13 showing a first anchor pin in a retracted position within the inner cavity of the screw body.
Figure 15:
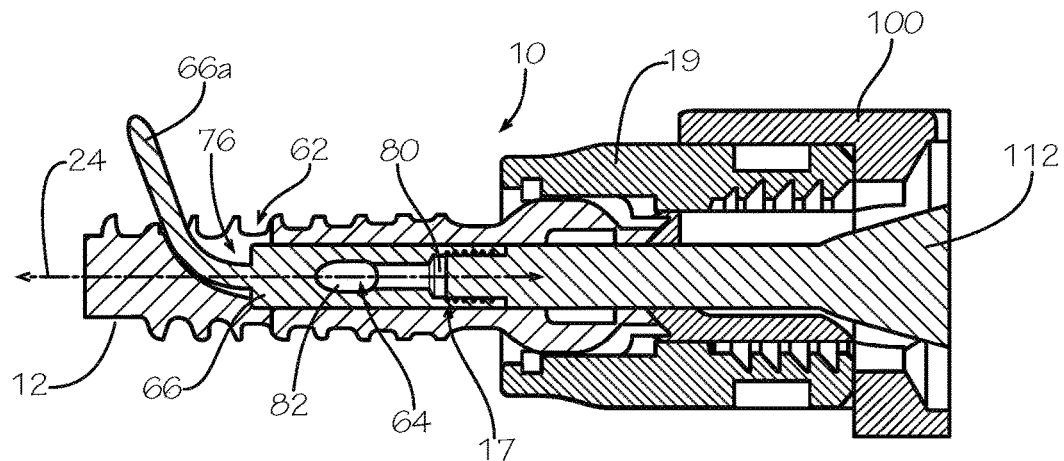
FIG. 15 is a cross sectional view of the bone screw of FIG. 14 showing the first anchor pin extended out of a first aperture after operation of the driver.
Figure 16:
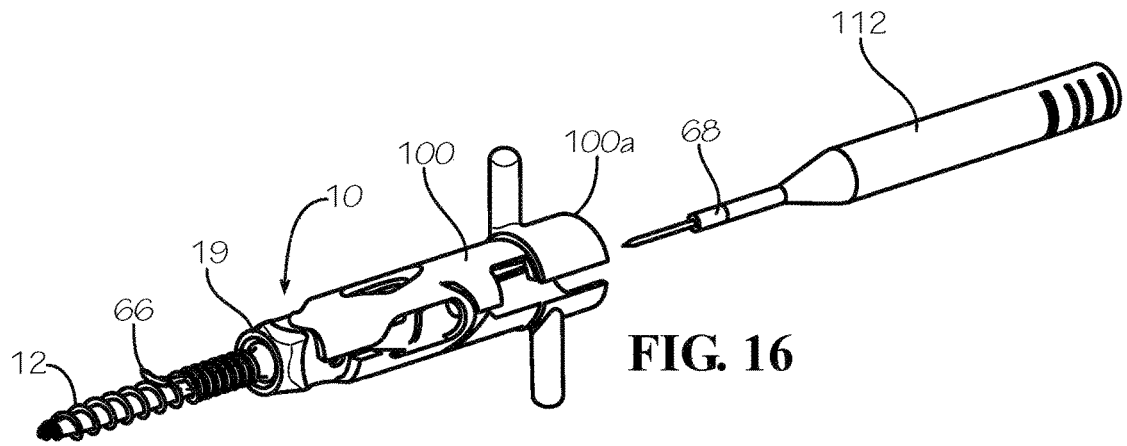
FIG. 16 is a perspective view of a second anchor pin connected to an inner shaft, the inner shaft being inserted through the outer sleeve and into the screw body.
Figure 17:
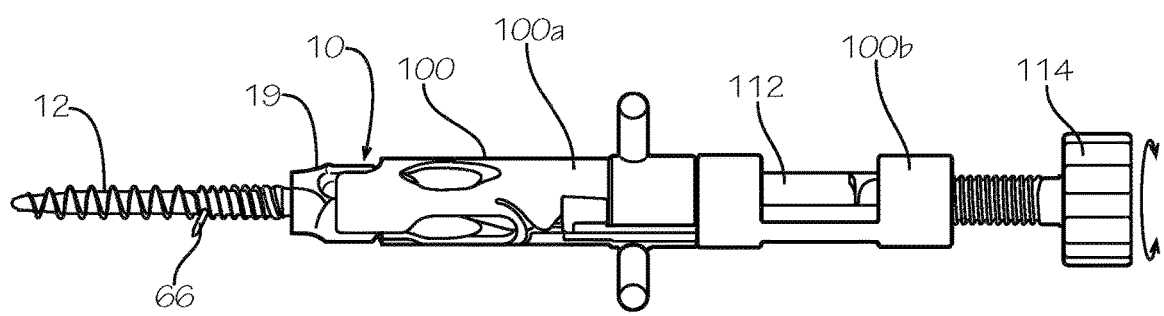
FIG. 17 is a side view of the second outer sleeve portion connected to the first outer sleeve portion over the inner shaft with the second anchor pin positioned in the screw body and the driver engaged with the inner shaft.

First and second anchor pins 66 and 68 can include straight and pointed distal ends 66a and 68a respectively, as shown in FIG. 6, which can be inserted into the inner cavity 17 and forced out of the first and second apertures 62 and 64 and into the patient's bone. The first and second anchor pins 66 and 68 can be guided through the first and second apertures 62 and 64 in various ways. In some embodiments, a first anchor guide channel 76 can extend between the first aperture 62 and the inner cavity 17, as shown in FIG. 14. The first anchor guide channel 76 can bend the first anchor pin 66 as the first anchor pin 66 passes through the first anchor guide channel 76 and extends out of the first aperture 62, as shown in FIG. 15. Anchor guide channel 76 can include a curved distal wall 78 which can bend the distal end 66a of the first anchor pin 66 as the first anchor pin 66 is inserted through the first anchor guide channel 76. As the distal end 66a of the first anchor pin 66 is bent through the first anchor guide channel 76, the distal end 66a of the first anchor pin 66 can extend through the first aperture 62 in the side wall 14 of the screw body 12 at an angle transverse to a longitudinal axis 24 of the screw body 12.

Figure 18:
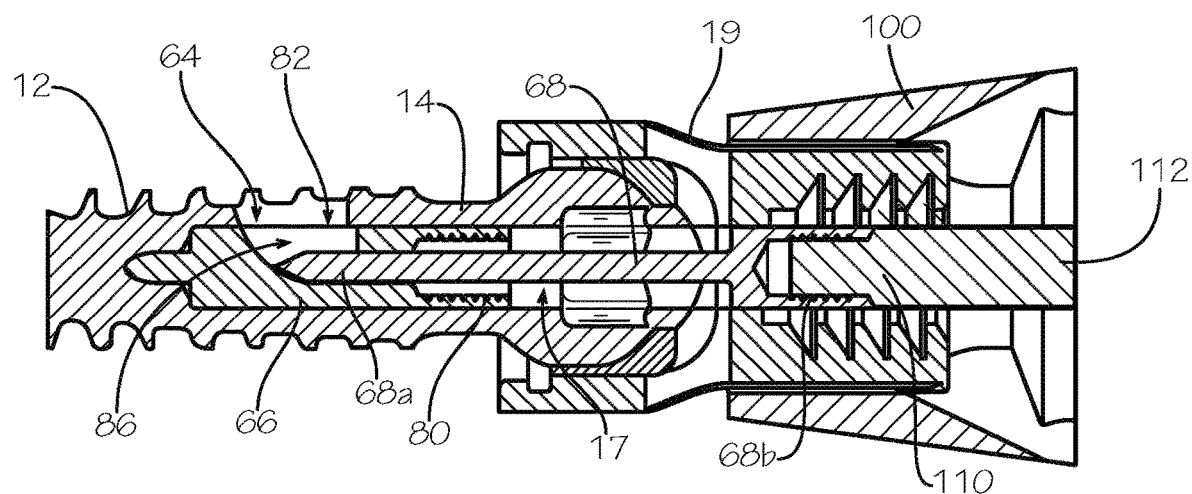
FIG. 18 is a cross sectional view of the bone screw of FIG. 17 showing a second anchor pin in a retracted position within the inner cavity of the screw body and the first anchor pin.
Figure 19:
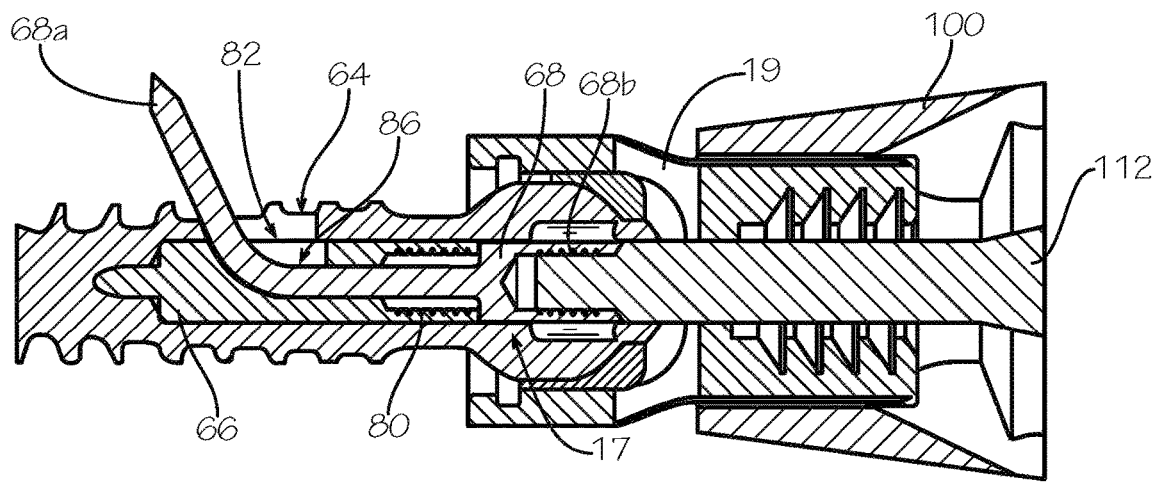
FIG. 19 is a cross sectional view of the bone screw of FIG. 18 showing the second anchor pin extended out of a second aperture after operation of the driver.
Figure 22:
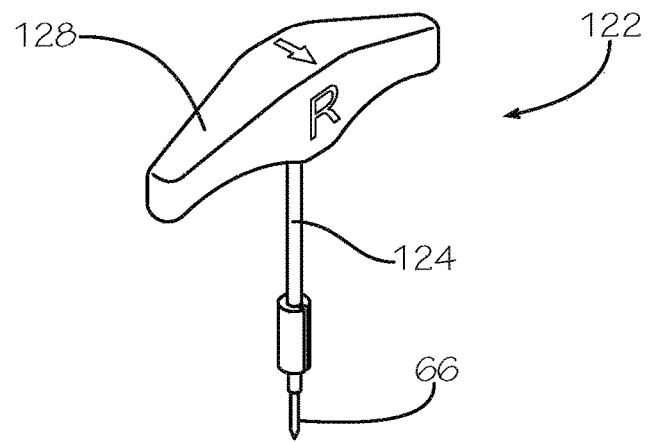
FIG. 22 is a perspective view of an embodiment of a tamping device for driving anchors through a bone screw.
Figure 23:
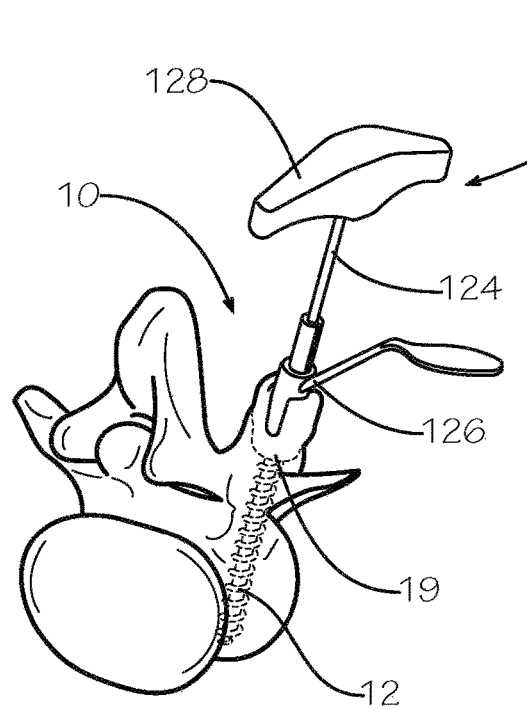
FIG. 23 is a perspective view of another bone screw device of the present disclosure utilizing a tamping device to drive anchor pins through an inner cavity of a screw body and into the patient's bone.
Figure 24:
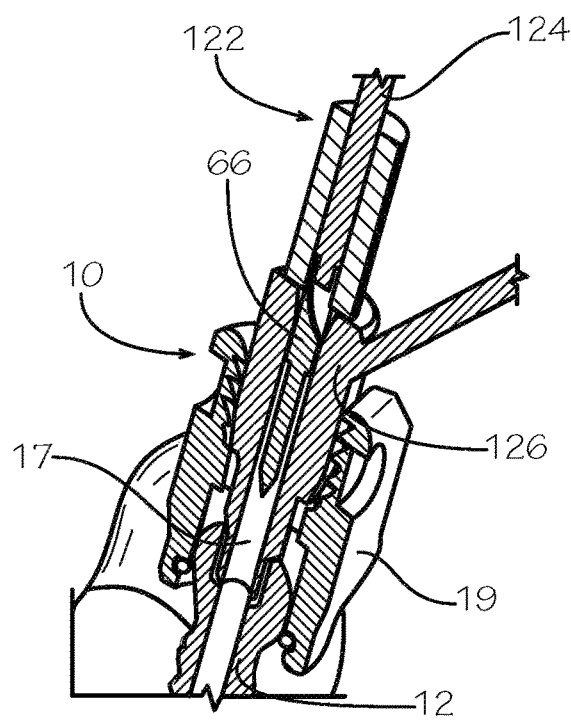
FIG. 24 is a detailed cross sectional view of the bone screw of FIG. 23.
Figure 25:
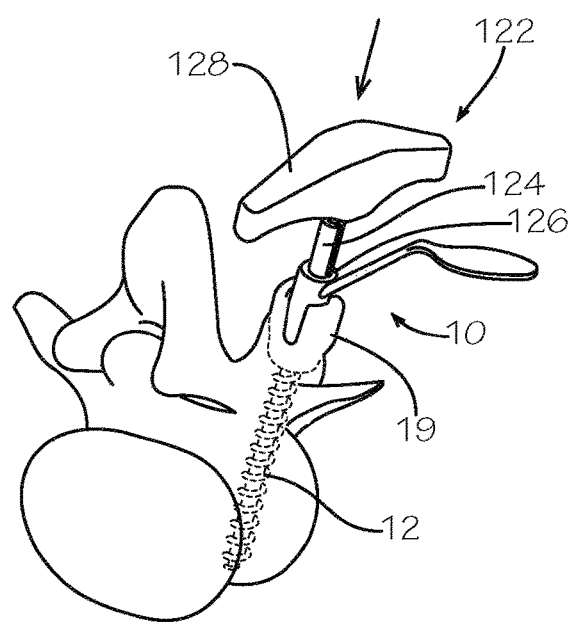
FIG. 25 is a perspective view of the bone screw of FIG. 23 with the tamping device tamped into the screw body.
Figure 26:
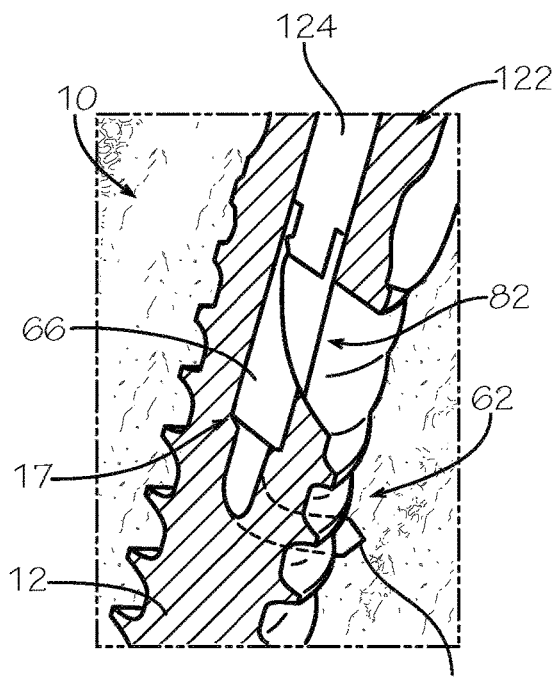
FIG. 26 is a detailed cross sectional view of the bone screw of FIG. 25 showing the first anchor pin in an extended position.
Figure 27:
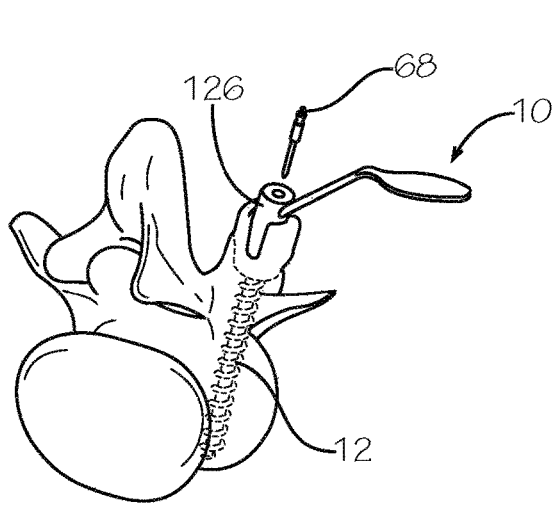
FIG. 27 is a perspective view of the bone screw of FIG. 23 showing a second anchor pin being inserted into the bone screw.
Figure 28:
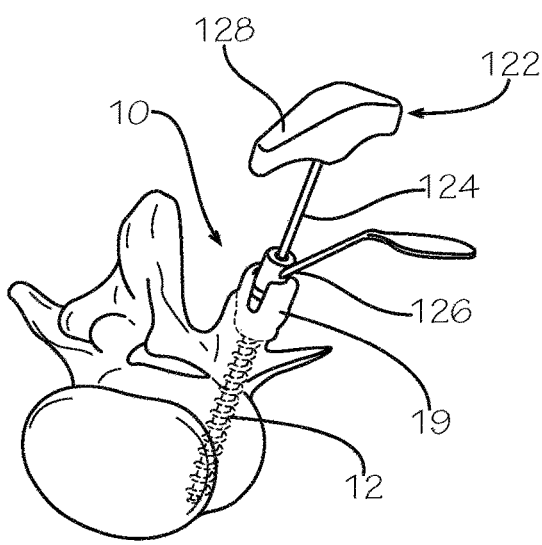
FIG. 28 is a perspective view of the bone screw of FIG. 27 showing the tamping device being inserted into the screw body over the second anchor pin.
Figure 29:
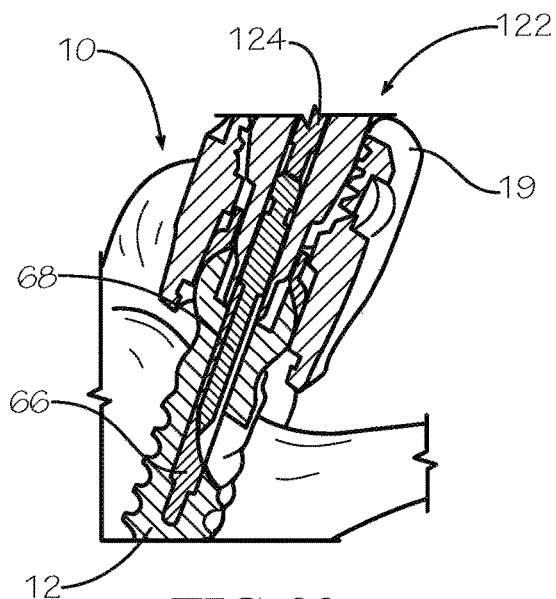
FIG. 29 is a cross sectional view of the bone screw of FIG. 28 showing the second anchor pin in a retracted position.
Figure 30:
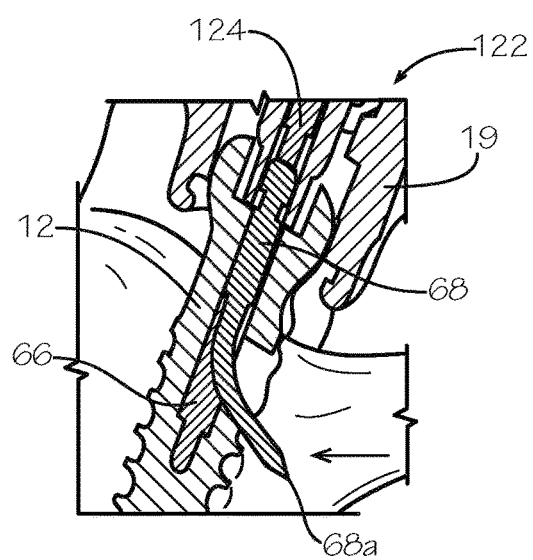
FIG. 30 is a cross sectional view of the bone screw of FIG. 28 showing the second anchor pin in an extended position.

In some embodiments, the first anchor pin 66 can include a central recess 80 extending into the first anchor pin from a proximal end 66b of the first anchor pin 66, as shown in FIG. 6. A second anchor pin aperture 82 can be defined through a side of the first anchor pin 66 and open to the central recess 80. As shown in FIG. 15, when the first anchor pin 66 is inserted into the screw body 12 and extended through the first aperture 62, the second anchor pin aperture 82 in the first anchor pin 66 can align with the second aperture 64 in the screw body 12. The second anchor pin 68 can be inserted into the inner cavity 17 of the screw body 12, extended through the first anchor pin 66 and out the second aperture 64 in the screw body 12, as shown in FIGS. 18-19. The second anchor pin 66 can extend through the central recess 80, through the second anchor pin aperture 82, and through the second aperture 68 in the screw body 12 to extend the second anchor pin 68 into the patient's bone.

In some embodiments, the first anchor pin 66 can include a second anchor guide channel 86 extending between the central recess 80 and the second anchor pin aperture 82. The second anchor guide channel 86 can bend the second anchor pin 68 as the second anchor pin 68 passes through the second anchor guide channel 86. The second anchor guide channel 86 therefore can guide the second anchor pin 68 from the central recess 80 to the second anchor pin aperture 82 and out the second aperture 64 in the screw body 12.

The second anchor pin 68 can thus be extendable through the second aperture 64 in the screw body 12 via the first anchor pin 66 in some embodiments. In other embodiments, first and second anchor guide channels can each be defined directly in the screw body 12. A first anchor guide channel can guide the first anchor pin 66 from the inner cavity 17 to the first aperture 62 in the screw body 12, and the second anchor guide channel can guide the second anchor pin 68 from the inner cavity through the second aperture 64 in the screw body 12, such that the second anchor pin 68 can pass through the screw body 12 independently of the first anchor pin 66.

Referring now to FIGS. 10-11, in some embodiments, the screw head 19 can be positioned on the screw body 12, the internal cavity 17 accessible through the screw head 19. A keyed feature 92 can be defined in the screw head 19. The keyed feature 92 can be used to drive the screw head 19 and thus the screw body 12 into the patient's bone prior to insertion of the anchor pins through the screw body 12 using a screw body driver having a distal end with a shape substantially corresponding to the shape of the keyed feature 92. The keyed feature 92 can be any suitable keyed feature having any suitable shape for driving the screw body 12, including but not limited to substantially square, hexagonal, star, or hex lobular shapes. In some embodiments, the first aperture 62 can be defined in a first side 90 of the screw body 12. The keyed feature 92 can have an asymmetrical portion 94 which can extend towards the first side 90 of the screw body 12 and toward the same side as the first aperture 62. As shown in FIG. 10, when looking into the internal cavity 17, the first anchor guide channel 76 extends toward the first aperture 62 in the first side 90 of the screw body 12.

Having a keyed feature 92 with an asymmetrical portion 94 that extends toward the same side as the first aperture 62 can allow a physician to ascertain the orientation of the first aperture 62 in the screw body 12 when the screw body 12 is installed or driven into a patient's bone. By examining the keyed feature 92, and particularly the asymmetrical portion 94 of the keyed feature 92, the physician can quickly determine the side 90 on which the first aperture 62 is located. When the physician inserts the first anchor pin 66 into the inner cavity 17, as shown in FIG. 11, the physician can use the asymmetrical portion 94 of the keyed feature 92 to properly align the first anchor pin 66 such that the second anchor pin aperture 82 will align with the second aperture 64 in the screw body 12 when the first anchor pin 66 is inserted and extended through the screw body 12.

The proper orientation of the first anchor pin 66 relative to the asymmetrical portion 94 of the keyed feature 92 can depend on the orientation of the first and second apertures relative to one another, as well as the orientation of the asymmetrical portion 94 of the keyed feature 92. For instance, in embodiments where the first and second apertures are oriented perpendicular to one another about a longitudinal axis 24 of the screw body, and the asymmetrical portion 94 of the keyed feature extends toward the same side as first aperture, the first anchor pin 66 would need to be inserted into the internal cavity 17 with the second anchor pin aperture 82 oriented perpendicularly to the asymmetrical portion 94 of the keyed feature 92. If the second aperture 64 is angularly spaced from the first aperture 62 about the longitudinal axis 24 of the screw body 12 in a clockwise direction when looking at the top of the screw head 19, then the second pin aperture 82 would need to be oriented perpendicular to the asymmetrical portion 94 of the keyed feature 94 in a clockwise direction. If the second aperture 64 is angular spaced from the first aperture 62 about the longitudinal axis 24 in a counter-clockwise direction, then the second pin aperture 82 would need to be oriented perpendicular to the asymmetrical portion 94 of the keyed feature 92 in a counter clockwise direction.

In other embodiments where the first and second apertures 62 and 64 are angularly spaced about the longitudinal axis of the screw body 12 at a non-perpendicular angle, the second anchor pin aperture 82 would need to be oriented at a congruent non-perpendicular angle with respect to the asymmetrical portion 94 of the keyed feature 92. In still other embodiments, the asymmetrical portion 94 of the keyed feature 92 can be oriented toward the same side as the second aperture 64, such that the second anchor pin aperture 82 would need to be aligned or oriented toward the same side as the asymmetrical portion 94 of the keyed feature 92 as the first anchor pin 66 is inserted into the inner cavity 17 of the screw body 12 to properly align the second anchor pin aperture 82 with the second aperture 64.

The asymmetrical portion 94 of the keyed feature 92 can also be utilized to position the screw within the patient's bone to ensure that the anchor pins extend from the bone screw 10 in a desired direction. For instance in a pedicle screw application, it is desirable for the anchor pins to extend away from the nerve stem within the spine of the patient to reduce the risk of damage to the nerve stem. The asymmetrical portion 94 of the keyed feature 92 can provide a visual indication of the direction in which the first and second anchor pins 66 and 68 will extend from the bone screw, so that the physician can use the keyed feature 92 to orient the screw body 12 in a proper orientation within the pedicle of the patient so that the anchors 66 and 68 will extend in a desirable direction generally away from the nerve stem.

As shown in FIGS. 21-21b, the pedicle screw 10 can be manufactured in both a left side orientation and a right side orientation. The screw head 12 can include a rod channel 96 defined through the screw head 19 for receiving a rod of a rod and screw spinal system. In practice, the rod channel 96 will be aligned generally parallel with the patient's spine. In some embodiments, in a left side pedicle screw 10a, shown in FIG. 21a, the asymmetrical portion 94 of the keyed feature 92 can extend perpendicularly to the rod channel 96 such that when the screw body 12 is inserted in a patient's left pedicle with the rod channel 96 generally parallel with the patient's spine and the asymmetrical portion 94 of the keyed feature 92 orientated away from the spine, the anchor pins when installed will extend to the left and upward, away from the nerve stem of the spine. In a right side pedicle screw 10b, shown in FIG. 21b, the asymmetrical portion 94 of the keyed feature 92 can extend parallel to the rod channel 96 such that when the screw body 12 is inserted in a patient's right pedicle with the rod channel 96 generally parallel with the patient's spine and the asymmetrical portion 94 of the keyed feature 92 orientated in an upward direction, the anchor pins when installed will extend upward and to the right, away from the nerve stem of the spine. The desired orientations of the asymmetrical portion of the keyed feature when the screw body 12 is positioned in one of the patient's bones will depend on the various relationships discussed above between the asymmetrical portion 94 of the keyed feature 92 and the apertures in the screw body 12.

Referring now to FIGS. 8-19, a process for installing the anchor pins 66 and 68 into the screw body 12 of FIG. 5 will be described. In some embodiments, once the screw body 12 is initially driven into a patient's bone via a screw body driver, an outer sleeve 100 can be engaged with the screw head 19. In some embodiments, the outer sleeve 100 can have a distal end with moveable tips 102. The movable tips 102 can be expanded to position the movable tips 102 and the outer sleeve 100 over the screw head 19, and the moveable tips 102 can be closed to engage the screw head 19. In some embodiments, the movable tips 102 can be resiliently biased toward a closed or contracted orientation via a living hinge 104. The proximal end of the outer sleeve 100 can include handles 106 which can be compressed in order to pivot the movable tips 102 about the living hinge 104 to an open or expanded orientation. When the handles 106 are released, the movable tips 102 can return to a closed orientation.

Referring now to FIG. 6, in some embodiments, the proximal end 66b of the first anchor pin 66 can include a first set of threads 108, and the proximal end 68b of the second anchor pin 68 can include a second set of threads 110. In some embodiments, each of the first and second sets of threads 108 and 110 can be internal threads. In other embodiments, each of the first and second sets of threads 108 and 110 can be external threads.

Referring again to FIGS. 9-19, an inner shaft 112 for installing the anchors can be connectable to the first anchor pin 66 and receivable within the outer sleeve 100. In some embodiments, the inner shaft 112 can be equipped with a distal end having threads that correspond to the first and second sets of threads 108 and 110 on the first and second anchor pins 66 and 68. The inner shaft 112 can be threaded onto or into the first anchor pin 66 to connect the inner shaft 112 to the first anchor pin 66. The first anchor pin 66 can then be inserted through the outer sleeve 100 and into the inner cavity 17 via the inner shaft 112. The distal end 66a of the first anchor pin 66 can positioned against the distal wall 78 of the first anchor guide channel 76, as shown in FIGS. 14.

Figure 13:
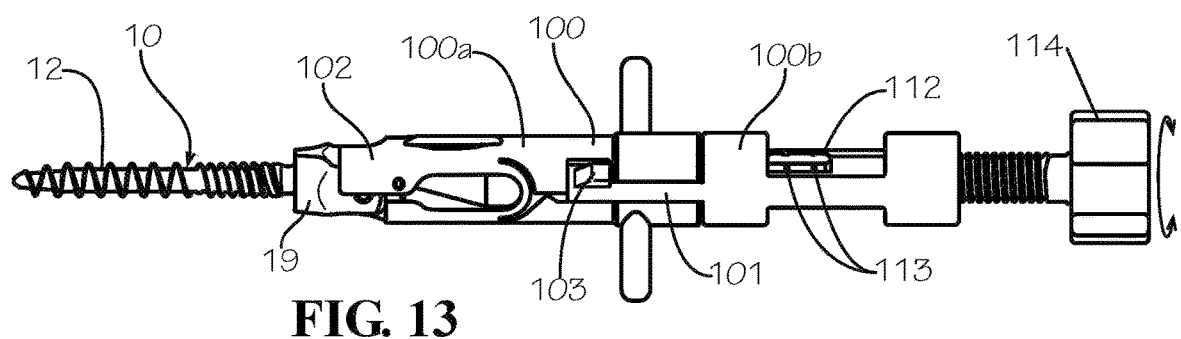
FIG. 13 is a side view of the bone screw of FIG. 9 showing a driver engaged with the second outer sleeve portion of the outer sleeve and engaging an inner shaft to drive the first anchor pin through a first aperture in the screw body.

A driver 114 can be engaged with the outer sleeve 100, as shown in FIG. 13. When the inner shaft 112 is positioned in the outer sleeve 100 and the first anchor pin 66 is positioned in the inner cavity 17, the driver 114 can be operable on the outer sleeve 100 to engage the inner shaft 112 and force the first anchor pin 66 through the first aperture 62, as shown in FIGS. 14-15.

Figure 12:
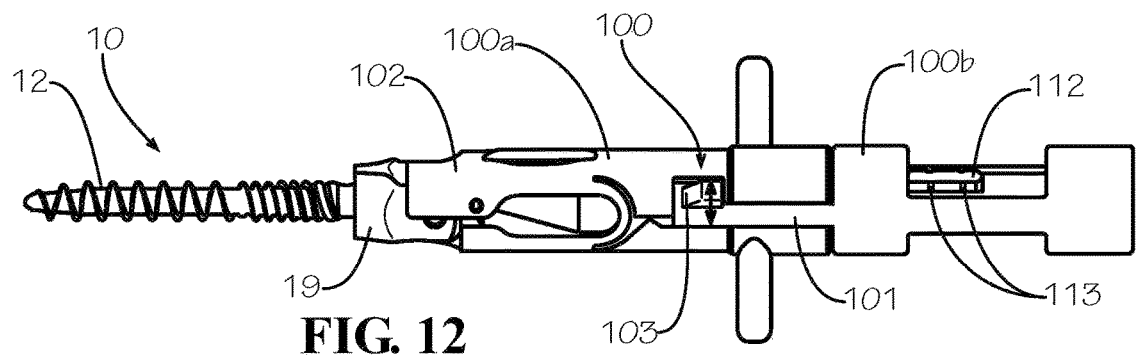
FIG. 12 is a side view of the bone screw of FIG. 8 with a second outer sleeve portion connected to a first outer sleeve portion over an inner shaft positioned in the first outer sleeve portion.

As shown in FIGS. 12-13, in some embodiments, the outer sleeve 100 can include a first outer sleeve portion 100a and a second outer sleeve portion 100b. The first outer sleeve portion 100a can be connectable to the screw head 19, and the second outer sleeve portion 100b can be securable to the first outer sleeve portion 100b, the driver 114 engageable with the second outer sleeve portion 100b. The first and second outer sleeve portions 100a and 100b are shown in FIGS. 12-13 as having a twist lock feature including a bidirectional groove 101 on the first outer sleeve portion 100a and a protrusion 103 on the second outer sleeve portion 100b. The second outer sleeve portion 100b can slide onto the first outer sleeve portion 100a engaged with the screw head 19 such that the protrusion 103 extends into the groove 101. The second outer sleeve portion 100b can be twisted such that the protrusion on the second outer sleeve portion 100b can move into a lateral portion of the bidirectional groove 101 on the first outer sleeve portion 100a to secure the first and second outer sleeve portions 100a and 100b together.

Having first and second outer sleeve portions 100a and 100b that can be securable together can allow the inner shaft 112 to be inserted into the first outer sleeve portion 100a, and the second outer sleeve portion 100b can subsequently be positioned over the inner shaft 112 and secured to the first outer sleeve portion 100a. A proximal end of the inner shaft 112 can extend beyond the first outer sleeve portion 100a when the first anchor pin 66 is positioned in the inner cavity 17 such that a physician can readily manipulate the first anchor pin 66 via the inner shaft 112. Once the first anchor pin 66 is in a desired orientation with the second anchor pin aperture 82 aligned with the second aperture 64, the second outer sleeve portion 100b can be secured to the first outer sleeve portion 100b over the inner shaft 112. The driver 114 can be engaged with the second outer sleeve portion 100b to drive the inner shaft 112 toward the inner cavity 17 to effectively force the first anchor pin 66 through the first anchor guide channel 76 and through the first aperture 62. Once the first anchor pin 66 is fully extended through the first aperture 66, the driver 114 can be removed from the second outer sleeve portion 100b, the second outer sleeve portion 100b can be removed from the first outer sleeve portion 100a, and the inner shaft 112 can be rotated the disengage the inner shaft 112 from the first anchor pin 66.

The inner shaft 112 can then be connected to the second anchor pin 68. The second anchor pin 68 can be inserted through the first outer sleeve portion 100a and into the inner cavity 17 via the inner shaft 112. The second outer sleeve portion 100b can be secured to the first outer sleeve portion 100b over the inner shaft 112. The driver 114 can be engaged with the second outer sleeve portion 100b, and the driver 114 can be operable to force the second anchor pin 68 through the first anchor pin 66, through the second anchor pin aperture 82 and out of the second aperture 64. Once the second anchor pin 68 is fully inserted into the patient's bone, the second outer sleeve portion 100b can be removed from the first outer sleeve portion 100a, the inner shaft 112 can be removed from the second anchor pin 68, and the first outer sleeve portion 100a can be removed from the screw head 19 to complete the installation of the anchors of the bone screw 10 into the patient's bone.

In some embodiments, the inner shaft 112 can include a plurality of guide markings 113, as shown in FIGS. 12-13. The guide markings 113 can denote desirable extension depths for respective anchors as the anchors are pushed into the screw body 12 by the inner shaft 112 as the driver 114 is actuated. The outer sleeve 100 can include a corresponding guide point, such as a window edge, such that when the desired guide marking 113 on the inner shaft 112 reaches the guide point on the outer sleeve 100, the guide marking 113 indicates that the desired extension depth for the respective anchor has been achieved.

In some embodiments, the driver 114 can be a jack screw which can threadingly engage the outer sleeve 100, and particularly the second outer sleeve portion 100b. The jack screw 114 can be rotated on the outer sleeve 100 to translate the jack screw 114 linearly with respect to the outer sleeve 100. As the jack screw 114 translates within the outer sleeve 100, the jack screw 114 can engage and push the inner shaft 112 such that the anchor pins 66 and 68 connected to the inner shaft 112 can be forced through the screw body 12 and out of respective apertures 62 and 64.

To remove an installed bone screw 10 from a patient, the same first and second outer sleeve portions 100a and 100b can be utilized. A removal shaft 116 can be connected to the second anchor pin 68 and subsequently to the first anchor pin 66 once the second anchor pin 68 is removed. In some embodiments, the removal shaft 116 can have a threaded distal end which can engage threads on the anchor pins. In other embodiments, the removal shaft 116 can be figured to grip a proximal end of the each anchor pin for removal. An embodiment of a removal shaft 116 is shown threadingly engaging a first anchor pin 66 in FIG. 20, though the removal shaft 116 could engage the second anchor pin in a similar fashion.

A removal force can be applied on the removal shaft 116 in a direction away from the patient and the screw body 12 to pull anchor pins connected to the removal shaft 116 out of the patient and out of the screw body 12. In some embodiments, a manual force can be applied to the removal shaft 116 such that a physician physically pulls each anchor pin out of the bone screw 10 via the removal shaft 116. In other embodiments, the removal shaft 116 can have a threaded proximal end, as shown in FIG. 20. A removal handle 118 with a threaded central bore 120 can threadingly engage the threaded proximal end of the removal shaft 116. The removal handle 118 can be rotated on the removal shaft 116 such that the removal handle 118 moves toward the screw body 12 and abuts the second outer sleeve portion 100b. As the removal handle 118 is further rotated, the second outer sleeve portion 100b will prevent further translation of the removal handle 118 which causes the removal handle 18 to apply a removal force on the removal shaft 116 in a direction away from the screw body 12. The removal force causes the removal shaft 116 to translate away from the screw body 12, which effectively causes the anchor pin connected to the removal shaft to be removed from the patient's bone and the screw body 12.

Another embodiment of an installation method for a bone screw 10 is shown in FIGS. 22-30. A tamp device 122 can be used in some embodiments to drive the anchor pins 66 and 68 through the screw body 12 and into the patient's bone. A first anchor pin 66 is shown being installed by the tamp device 122 in FIGS. 22-26. The tamp device 122 can include a tamp rod 124 having a distal end configured to engaged a proximal end of the first anchor pin 68. The distal end of the tamp rod 124 can be sized to produce a slight interference fit with the central recess 80 of the the first anchor pin 66 to selectively retain the first anchor pin 66 on the tamp rod 124. In some embodiments, a tamp rod guide 126 can be positioned on the screw head 19, the tamp rod guide 126 configured to receive and support the tamp rod 124 as the tamp rod 124 is used to drive the first anchor pin 66 into the patient's bone. The first anchor pin 66 and the tamp rod 124 can be inserted through the tamp rod guide 126 and into the inner cavity 17 of the screw body 12.

The tamp device 122 can include a tamp head 128 positioned on a proximal end of the tamp rod 124. The tamp rod 124 can be hammered or tamped via the tamp head 128 to drive the first anchor pin 66 into the patient's bone. As shown in FIGS. 27-30, a similar procedure can be performed with the second anchor pin 68, the second anchor pin 68 being dropped through the tamp rod guide 126 and into the inner cavity 17, the tamp rod 124 being inserted through the tamp rod guide 126 over the second anchor pin 68, the tamp rod 124 being hammered or tamped via the tamp head 128 to drive the second anchor pin 68 through the first anchor pin 66 and through the second aperture 64.

Figure 31:
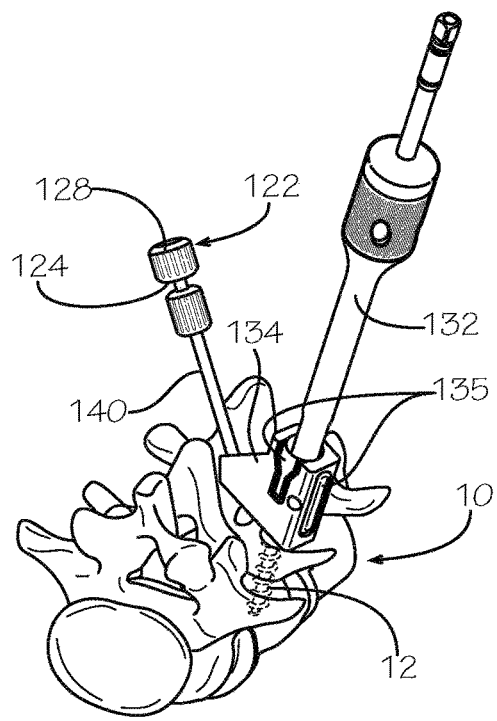
FIG. 31 is a perspective view of another embodiment of a bone screw of the present disclosure.
Figure 32:
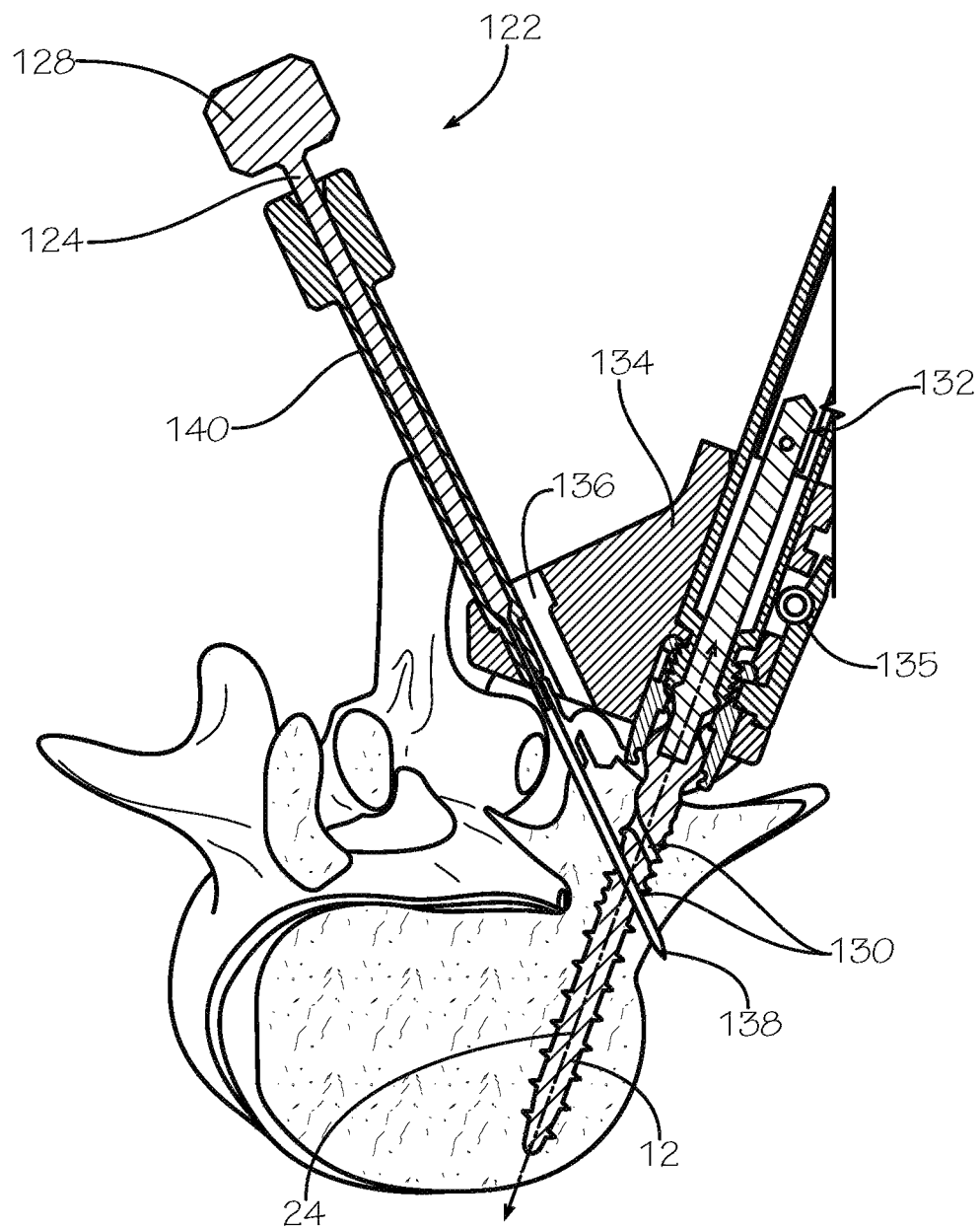
FIG. 32 is a detailed cross sectional view of the bone screw of FIG. 31.

Another embodiment of a bone screw 10 of the present disclosure is shown in FIGS. 31-32. The screw body 12 can have one or more angled passages 130 extending through the screw body 12 in a direction transverse to the longitudinal axis 24 of the screw body 12. A screw body driver 132 for driving the screw body 12 into the patient's bone can include a pin guide member 134. The pin guide member 134 can include angular guide slots 136. The pin guide member 134 can be moved along the screw body driver 132 to move the pin guide member 134 to a position wherein the angular guide slots 136 align with corresponding angled passages 130 in the screw body 12. A spring clamp 135 can selectively secure the pin guide member 134 along the screw body driver 132.

Once the screw body 12 is driven into the patient's bone via the screw body driver 132, the pin guide member 134 can be moved so that the angled guide slots 136 align with the angles passages 130. Elongate anchor pins 138 can be inserted through the angle guide slots 136 in the pin guide member 134, through the patient's bone, through the angled passages 130, and into the patient's bone on an opposite side of the screw body 12 to further purchase and fixate the bone screw 10 within the patient's bone. In some embodiments, a pin guide sleeve 140 can be inserted into the guide slots 136 to guide corresponding elongated anchor pins 138 through the guide slots 136 during installation of the elongated anchor pins 138. An elongated anchor pin 138 can be inserted into the pin guide sleeve 140, and a tamp rod 124 of a tamp device 122 can be inserted into the pin guide sleeve 140 over the elongated anchor pin 138. The tamp device 122 can be hammered or tamped to drive the elongated anchor pin 138 through the pin guide member 134, through the patient's bone, through a corresponding angled passage 130 in the screw body 12, and into the patient's bone on the opposing side of the screw body 12.

The various bone screws 10 disclosed herein can be utilized for any patient where the surgeon perceives risk of acute or delayed screw pullout or is at risk of pseudo arthrosis, such as patients with osteoporosis or osteopenia; deformity correction surgeries where large forces may be placed on bone screws to achieve bone realignment; spondylolisthesis reduction where high screw pullout force loads are placed on pedicle screws; patients who smoke or are at increased risk of pseudo arthrosis; patients on hemodialysis, chronic steroids, or any form of iatrogenic poor bone quality. Those of skill in the art will recognize that certain embodiments of the invention disclosed herein can be indicated for use in other various anatomy locations within the body, including but not limited to, the spine, long-bones, and pelvis bones.

Although there have been described particular embodiments of the present invention of a new and useful BONE FIXATION SCREW WITH DEPLOYABLE ANCHORS it is not intended that such references be construed as limitation upon the scope of this invention except as set forth in the following claims.

What is claimed is:

1. A screw device for implantation into a bone of a patient comprising:
   a screw body having an outer surface and an inner cavity;
   a plurality of outer screw threads extending around the outer surface of the screw body;
   a plurality of apertures defined through the outer surface, the plurality of apertures open to the inner cavity of the screw body; and
   a plurality of anchors, each anchor out of a corresponding aperture in the screw body from the inner cavity of the screw body, wherein the plurality of anchors includes:
      a first anchor pin extendable out of a first aperture of the plurality of apertures from the inner cavity, the first anchor pin including:
         a central recess extending into the first anchor pin from a proximal end of the first anchor pin, and
         a second anchor pin aperture defined through a side of the first anchor pin and open to the central recess; and
      a second anchor pin extendable out of a second aperture of the plurality of apertures from the inner cavity, wherein the second anchor pin is extendable though the central recess, through the second anchor aperture, and through the second aperture in the screw body when the first anchor pin is extended through the first aperture, such that the second anchor pin is extendable through the second aperture in the screw body via the first anchor pin.

2. The device of claim 1, wherein:
   the first anchor is extendable out of the screw body in a first radial direction; and
   the second anchor is extendable out of the screw body in a second radial direction;
   wherein the first and second radial directions are oriented at an angle with respect to one another.

3. The device of claim 2, wherein the first and second radial directions are perpendicular to one another.

4. The device of claim 1, wherein:
   the screw body has a longitudinal axis; and
   each anchor extends from the corresponding aperture in a direction that is transverse to the longitudinal axis of the screw body.

5. The device of claim 1, wherein the plurality of anchors are movable between a retracted position within the inner cavity to an extended position, the anchors extending out of corresponding apertures in the extended position.

6. A screw device for implantation into a bone of a patient comprising:
   a screw body having an outer surface and an inner cavity;
   a plurality of outer screw threads extending around the outer surface of the screw body;
   a first aperture defined in the outer surface of the screw body, the first aperture open to the inner cavity;
   a second aperture defined in the outer surface of the screw body, the second aperture open to the inner cavity;
   a first anchor pin extendable out of the first aperture from the inner cavity, wherein the first anchor pin includes:
      a central recess extending into the first anchor pin from a proximal end of the first anchor pin, and
      a second anchor pin aperture defined through a side of the first anchor pin and open to the central recess; and a second anchor pin extendable out of the second aperture from the inner cavity, wherein the second anchor pin is extendable though the central recess, through the second anchor pin aperture, and through the second aperture in the screw body when the first anchor pin is extended through the first aperture, such that the second anchor pin is extendable through the second aperture in the screw body via the first anchor pin.

7. The device of claim 6, further comprising a first anchor guide channel extending between the first aperture and the inner cavity, the first anchor guide channel bending the first anchor pin as the first anchor pin passes through the first anchor guide channel and extends out of the first aperture.

8. The device of claim 7, further comprising a second anchor guide channel defined in the first anchor pin and extending between the central recess and the second anchor pin aperture, the second anchor guide channel bending the second anchor pin as the second anchor pin extends through the second anchor guide channel and through the second aperture.

9. The device of claim 6, further comprising:
the first aperture positioned on a first side of the screw body;
a screw head positioned on the screw body, the inner cavity accessible through the screw head; and
a keyed feature defined in the screw head for driving the screw body, the keyed feature having an asymmetrical portion oriented toward the first side of the screw body.

10. The device of claim 6, wherein:
the screw body includes a longitudinal axis; and
the first and second apertures are angularly spaced from each other on the screw body about the longitudinal axis at an angle of about 90 degrees.

11. The device of claim 10, wherein:
the first anchor pin is extendable out of the first aperture in a first direction;
the second anchor pin is extendable out of the second aperture in a second direction; and
the first and second directions are oriented radially perpendicular to one another.

12. The device of claim 6, wherein:
the first anchor pin has a first anchor proximal end having a first set of internal threads; and
the second anchor pin has a second anchor proximal end having a second set of internal threads.

13. The device of claim 6, further comprising:
a screw head positioned on the screw body, the inner cavity accessible through the screw head;
an outer sleeve engageable with the screw head;
an inner shaft connectable to the first anchor pin and receivable within the outer sleeve; and
a driver engageable with the outer sleeve;
wherein when the outer sleeve is engaged with the screw head, the inner shaft is connected to the first anchor pin and received in the outer sleeve with the first anchor pin in the inner cavity, and the driver is engaged with the outer sleeve, the driver is operable to engage the inner shaft and force the first anchor pin through the first aperture.

14. The device of claim 13, wherein:
the inner shaft is connectable to the second anchor pin; and
when the first anchor pin is extended out of the first aperture, the outer sleeve is engaged with the screw, the inner shaft is connected to the second anchor pin and received in the outer sleeve with the second anchor pin in the inner cavity; and
the driver is engaged with the outer sleeve, the driver is operable to engage the inner shaft to force the second anchor pin through the second aperture.

15. The device of claim 13, wherein the driver is a jack screw that can threadingly engage the outer sleeve, the jack screw rotatable to translate the jack screw relative to the outer sleeve to engage the inner shaft.

16. The device of claim 13, wherein the outer sleeve further comprises:
a first outer sleeve portion engageable with the screw head; and
a second outer sleeve portion securable to the first outer sleeve portion, the driver engageable with the second outer sleeve portion.

17. The device of claim 13, wherein the inner shaft can include a plurality of insertion depth guide markings.

18. A screw device for implantation into a bone of a patient comprising:
a screw body having an outer surface and an inner cavity;
a plurality of outer screw threads extending around the outer surface of the screw body;
a first aperture defined in the outer surface of the screw body, the first aperture open to the inner cavity;
a second aperture defined in the outer surface of the screw body, the second aperture open to the inner cavity;
a first anchor pin insertable through the inner cavity and extendable out of the first aperture; and
a second anchor pin insertable through the inner cavity and extendable through the first anchor pin and out of the second aperture when the first anchor pin is extended through the first aperture.

19. The device of claim 18, wherein the first and second anchor pins are extendable out of the screw body beyond the outer screw threads on the screw body.

* * * * *